United States Patent [19]

Alminger et al.

[11] Patent Number: 5,215,974
[45] Date of Patent: Jun. 1, 1993

[54] CERTAIN PYRIDYL[(METHYLTHIO- OR METHYL SULFINYL)-2 BENZIMIDAZOL-2-YL]N-METHYL PHOSPHONATES USEFUL FOR TREATING GASTRIC-ACID SECRETION RELATED DISEASES

[75] Inventors: Tomas B. Alminger, Lindome; Rolf A. Bergman, Molndal, both of Sweden; Bundgaard H., Horsholm, Denmark; Per L. Lindberg, Askim; Gunnel E. Sunden, Gothenburg, both of Sweden

[73] Assignee: Aktiebolaget Hassle, Molndal, Sweden

[21] Appl. No.: 654,394

[22] Filed: Feb. 8, 1991

Related U.S. Application Data

[63] Continuation of Ser. No. 380,040, Oct. 10, 1989, abandoned, which is a continuation of Ser. No. 297,606, Jan. 13, 1989, abandoned, which is a continuation-in-part of Ser. No. 199,263, May 18, 1988, abandoned.

[30] Foreign Application Priority Data

| Nov. 21, 1986 | [SE] | Sweden | 8604998 |
| Dec. 23, 1986 | [SE] | Sweden | 8605551 |
| Oct. 16, 1987 | [SE] | Sweden | 8704049 |
| Nov. 20, 1987 | [WO] | PCT Int'l Appl. | PCT/SE87/00546 |

[51] Int. Cl.$^5$ .................. C07F 9/58; A61K 31/675

[52] U.S. Cl. ..................... 514/80; 514/89; 546/22; 546/271

[58] Field of Search ............. 546/22; 514/89, 80

[56] References Cited

PUBLICATIONS

Bundgaard, H., *Design of Prodrugs*, pp. 7-9, 21-24, Elsevier, Amsterdam, 1985.

Juliano, R. L., *Drug Delivery Systems*, pp. 124-128, Oxford University Press, New York, 1980.

*Primary Examiner*—Alan L. Rotman
*Attorney, Agent, or Firm*—White & Case

[57] ABSTRACT

Novel compounds of the formula

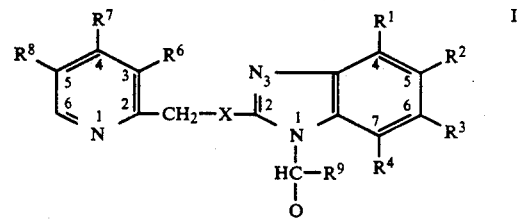

pharmaceutical compositions containing such compounds as active ingredient, and the use of the compounds in medicine for treating gastric acid related diseases such as gastritis, gastric ulcer, duodenal ulcer and reflux esophagitis.

22 Claims, No Drawings

CERTAIN PYRIDYL[(METHYLTHIO- OR METHYL SULFINYL)-2 BENZIMIDAZOL-2-YL]N-METHYL PHOSPHONATES USEFUL FOR TREATING GASTRIC-ACID SECRETION RELATED DISEASES

This application is a continuation of application Ser. No. 380,040, filed Oct. 10, 1989 now abandoned which is a continuation of application Ser. No. 297,606, filed Jan. 13, 1989 now abandoned which is a continuation-in-part of application Ser. No. 199,263, filed May 18, 1988 now abandoned.

FIELD OF THE INVENTION

The object of the present invention is to provide novel compounds, and therapeutically acceptable salts thereof, which inhibit exogenously or endogenously stimulated gastric acid secretion and thus can be used in the prevention and treatment of peptic ulcer.

The present invention relates to the use of the compounds of the invention, especially therapeutically acceptable salts thereof, for inhibiting gastric acid secretion in mammals and man. In a more general sense, the compounds of the invention may be used for prevention and treatment of gastrointestinal inflammatory diseases, and gastric acid-related diseases in mammals and man, such as gastritis, gastric ulcer, duodenal ulcer, and reflux esophagitis. Furthermore, the compounds may be used for treatment of other gastrointestinal disorders where gastric antisecretory effect is desirable e.g. in patients with gastrinomas, and in patients with acute upper gastrointestinal bleeding. They may also be used in patients in intensive care situations, and pre-and post-operatively to prevent acid aspiration and stress ulceration. The invention also relates to pharmaceutical compositions containing at least one compound of the invention, or a therapeutically acceptable salt thereof, as active ingredient. In a further aspect, the invention relates to processes for preparation of such new compounds, to novel intermediates in the preparation of the compounds of the invention, and to the use of the active compounds for the preparation of pharmaceutical compositions for the medical use indicated above.

PRIOR ART AND BACKGROUND OF THE INVENTION

Benzimidazole derivatives intended for inhibiting gastric acid secretion are disclosed in numerous patent documents. Among these can be mentioned GB 1 500 043, GB 1 525 958, U.S. Pat. No. 4,182,766, EP 0 005 129, and BE 890 024. Benzimidazole derivatives proposed for use in the treatment or prevention of special gastrointestinal inflammatory diseases are disclosed in EP-A-0 045 200. N-substituted 2-(pyridylalkylenesulfinyl)benzimidazoles are disclosed in EP-A-0 176 308.

For certain pharmaceutical usage forms there is a great need for high water solubility of the compound to be used. For instance, for intravenous and intramuscular injection formulations, the dose is to be dissolved in a small volume of an aqueous medium. This, of course, requires a high aqueous solubility. However, a high aqueous solubility is often a great advantage also in other cases e.g. for oral formulations.

The compounds in the prior art generally have a low water solubility, which does not admit manufacture of such highly concentrated water solution which are needed for intravenous and intramuscular injections. For example the compounds presented in the European patent application, publication no. 0176308, disclosing N-substituted benzimidazole derivatives, have low water solubility and are thus not suitable for the above-mentioned parenteral use.

THE INVENTION

It has been found that the compounds of the following formula I are effective as inhibitors of gastric acid secretion in mammals and man, and that the said compounds I exhibit an unexpectedly high solubility in water compared with compounds in the prior art.

The compounds of the invention wherein X is SO generally show higher chemical stability in water solutions at the pH where they exhibit optimal stability compared to the corresponding compounds without the N-1 substitution, at the same pH. Some of the compounds of the invention show exceedingly high chemical stability in solution. The compounds of the formula I are therefore particularly suitable for parenteral, especially intravenous and intramuscular administration. The high solubility and chemical stability also render the compounds of the invention suitable for other administration routes, such as for instance oral and rectal administration.

The compounds of the invention are of the following formula I:

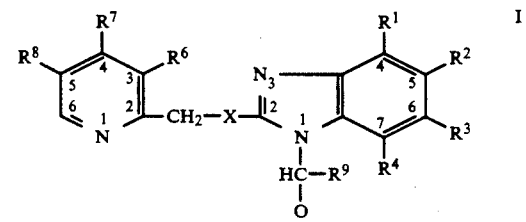

and physiologically acceptable salts thereof, wherein
X is -S- or -SO-;
$R^1$, $R^2$, $R^3$ and $R^4$, which are the same or different, are
(a) H
(b) alkyl containing 1-8, especially 1-6 carbon atoms;
(c) alkoxy containing 1-8, especially 1-6 carbon atoms
(d) alkoxyalkyl containing 1-3 carbon atoms in each alkyl part
(e) alkoxyalkoxy containing 1-3 carbon atoms in each alkyl part
(f) halogen
(g) —CN,
(h) —CF$_3$
(i) —NO$_2$
(j) —COR$^{10}$
(k) alkylthio containing 1-6 carbon atoms in the alkyl part,
(l) alkylsulfinyl containing 1-7 carbon atoms in the alkyl part
(m) aryl-thio, -sulfinyl, -sulfonyl, -sulfonyloxy, -oxysulfonyl, -sulfonamido or -aminosulfonyl, whereby each aryl group optionally is substituted by 1-3 substituents, the same or different and selected from halogen, CF$_3$, (1-5C) alkyl and (1-5C)alkoxy
(n) arylalkyl or arylalkoxy, containing 1-6 carbon atoms in the alkyl and alkoxy parts, respectively whereby the aryl part optionally is substituted by 1-3 substituents, the same or different and selected from halogen, $CF_3$, (1-5C)alkyl and (1-5C)alkoxy (o) aryl or aryloxy, whereby each aryl group optionally is substituted by 1-3 substituents, the same or different and selected from halogen, $CF_3$, (1-5C)alkyl and (1-5C)alkoxy (p) haloalkoxy containing 1-6 carbon atoms and 1-11, especially 1-6 halogen atoms (q) hydroxyalkyl containing 1-6 carbon atoms (r) $R^1$ and $R^2$, $R^2$ and $R^3$ or $R^3$ and $R^4$ together with the adjacent carbon atoms in the benzimidazole ring form one or more 5-, 6- or 7-membered rings, which each may be saturated or unsaturated and may contain 0-3 hetero atoms selected from N, S and O, and whereby each ring may be optionally substituted with 1-10, suitably 1-6, or 1-4 substituents selected from alkyl groups with 1-3 carbon atoms and halogen, or two or four of the mentioned substituents together form one or two oxo groups

whereby if $R^1$ and $R^2$, $R^2$ and $R^3$ or $R^3$ and $R^4$ together with the adjacent carbon atoms in the benzimidazole ring form two rings the rings may be condensed with each other;

D is

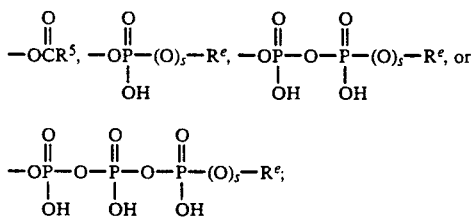

$R^5$ is

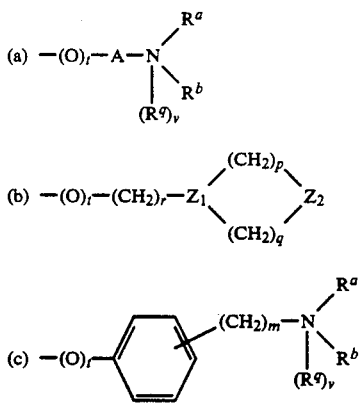

wherein the substituent on the phenyl group is in meta- or in para-position,

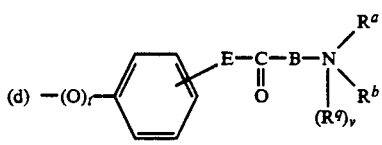

wherein the substituent on the phenyl group is in meta- or in para-position,

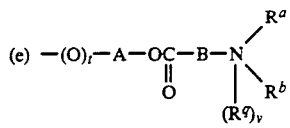

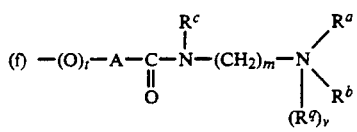

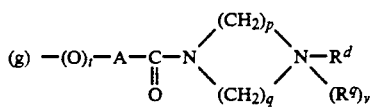

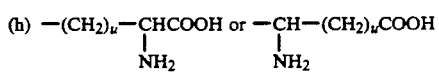

(i) mono- or dicarboxy-substituted 2-, 3-, or 4-pyridinyl or mono- or dicarboxy-substituted 2-, 3-, or 4-pyridinyloxy

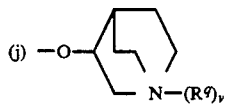

$R^6$ is
(a) H
(b) alkyl containing 1-8, especially 1-6 carbon atoms
(c) alkoxy containing 1-8, especially 1-6 carbon atoms
(d) halogen $R^8$ is
(a) H
(b) alkyl containing 1-8, especially 1-6 carbon atoms
(c) alkoxy containing 1-8, especially 1-6 carbon atoms
(d) halogen
(e) arylalkyl containing 1-4 carbon atoms in the alkyl part $R^7$ is
(a) H
(b) alkyl containing 1-7 carbon atoms
(c) alkoxy containing 1-7 carbon atoms
(d) alkoxyalkyl containing 1-3 carbon atoms in each alkyl part
(e) alkoxyalkoxy containing 1-3 carbon atoms in each alkyl part
(f) aryloxy, whereby the aryl group optionally is substituted by 1 or 2 substituents, the same or different and selected from halogen, $CF_3$, (1-3C)alkyl or (1-3C)alkoxy
(g) arylalkyl or arylalkoxy containing 1-7 carbon atoms in the alkyl and alkoxy part, respectively, whereby the aryl part optionally is substituted by 1 or 2 substituents, the same or different and selected from halogen, $CF_3$, (1-3C)alkyl and (1-3C)alkoxy
(h) alkenyloxy containing 1-7 carbon atoms in the alkenyl part
(i) alkynyloxy containing 1-7 carbon atoms in the alkynyl part (j) alkylthio containing 1-7, preferably 1-3 carbon atoms in the alkyl part
(k) arylthio or arylalkylthio containing 1-3, preferably 1 carbon atom in the alkyl part
(l) dialkylamino containing 1-7, preferably 1-3 carbon atoms in each of the alkyl parts
(m) morpholino
(n) piperidino
(o) N-methylpiperazino
(p) pyrrolidino
(q) fluoroalkoxy containing 2-5 carbon atoms and 1-9 fluorine atoms
or $R^6$ and $R^7$, or $R^7$ and $R^8$ together with the adjacent carbon atoms in the pyridine ring form a 5- or 6-membered, saturated or unsaturated ring, which may optionally contain an oxygen, sulphur or an optionally alkylated nitrogen atom;

$R^9$ is
(a) H
(b) alkyl containing 1-4 carbon atoms;

$R^{10}$ is
(a) alkyl containing 1-6 carbon atoms
(b) alkoxy containing 1-6 carbon atoms
(c) aryl;

A is
(a) straight or branched (1-8C)alkylene
(b) (3-7C) cycloalkylene
(c) (4-9C)alkylene containing a cycloalkylene group;

B is
(a) —$(CH_2)_m$—

(b) 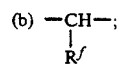

E is (a) —O— or (b) —NH—;

$Z_1$ is (a) 

(b) 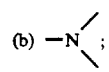

$Z_2$ is
(a) —$CH_2$—
(b) —$NR^d(R^q)_v$—
(c) —S—
(d) —O—;

$R^a$, $R^b$, $R^c$, $R^d$ and $R^q$ are the same or different and selected from
(a) H
(b) (1-6C)alkyl;

$R^e$ is
(a) H
(b) (1-6C)alkyl
(c) aryl (0-3C)alkyl whereby the aryl group optionally is substituted by 1-3 substituents, the same or different and selected from halogen, $CF_3$, $NO_2$, (1-5C)alkyl and (1-5C)alkoxy;

$R^f$ is the side chain of an amino acid;
m is an integer 0, 1, 2, 3, 4, 5, 6, 7 or 8;
p is an integer 1, 2, 3 or 4;
q is an integer 1, 2, 3 or 4;
r is an integer 0, 1, 2, 3, 4, 5, 6, 7, 8;
s is an integer 0 or 1;
t is an integer 0 or 1;
u is an integer 1 or 2;
v is an integer 0 or 1;
and whereby the group D when containing one or two carboxylic acid groups or a phosphorous-containing group preferably is in the form of a mono-, di-, tri- or tetra-ionic salt containing a physiologically acceptable counter cation, and when containing an amino function may be in the form of an ammonium salt (v=1; the nitrogen is positively charged) having a physiologically acceptable counter anion, or in the form of a free amine (v=0). In the case when $R^5$ is the chain of aspartic acid (u=1) or glutamic acid (u=2) as in h), $R^5$ may also be in a zwitter-ionic form; with the provisos that (1) A is (3-7C) cycloalkylene or (4-9C) alkylene containing a cycloalkylene group when the following conditions are fulfilled simultaneously:

(a) $R^5$ is

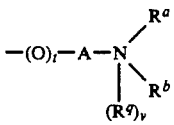

(b) $R^a$ is H, (1-3C)alkyl
(c) $R^b$ is H, (1-3C)alkyl
(d) v is 0, or $R^q$ is H and v is 1

(2) Either or both of $R^6$ and $R^8$ is halogen when $R^7$ is dialkylamino, morpholino, piperidino, N-methylpiperazino or pyrrolidino.

It should be understood that the expressions "alkyl" and "alkoxy" include straight, branched, and cyclic structures including cycloalkylalkyl and cycloalkylalkoxy, respectively.

The number of carbon atoms in a given radical is in this specification either expressly stated or given in abbreviated form within parentheses such as (1-3C)alkyl.

The compounds of the invention that are sulfoxides have an asymetric centre in the sulfur atom, i.e. these compounds exist as two optical isomers (enantiomers), or if they also contain one or more asymmetric carbon atoms the compounds have two or more diastereomeric forms, each existing in two enantiomeric forms.

Both the pure enantiomers, racemic mixtures (50% of each enantiomer) and unequal mixtures of the two are within the scope of the present invention. It should be understood that all the diasteromeric forms possible (pure enantiomers or racemic mixtures) are within the scope of the invention.

The compounds of the invention that are sulfides (X=S) may be asymmetric due to one or more asymmetric carbon atoms, as described above. The different diastereomeric forms possible as well as the pure enantiomers and racemic mixtures are within the scope of the invention.

Preferred groups of compounds of the formula I are:
1. Compounds wherein X is —SO—.
2. Compounds wherein X is —S—.
3. Compounds wherein $R^1$, $R^2$, $R^3$ and $R^4$ are the same or different and selected from hydrogen, (1-2C)alkyl, (5-6C)cycloalkyl, (1-4C)alkoxy, (1-2C)alkoxy(-1-2C)alkyl, (1-2C)alkoxy(1-2C)alkoxy, halogen, $CF_3$, (2-4C)alkanoyl, arylcarbonyl, (1-2C)alkoxycarbonyl, aryl(1-3C)alkoxy, aryl, halo(1-4C)alkoxy, hydroxy(-1-4C)alkyl, (2-4C)alkanoyl(1-3C)alkyl, or wherein R² and R³ together with the ring carbons form a 5- or 6-membered saturated, oxygen-containing or carbocyclic, ring, optionally substituted by 1-6 substituents, the same or different and selected from halogen, (1-2C)alkyl, or two of the substituents together form an oxo group.

4. Compounds wherein R¹, R², R³ and R⁴ are the same or different and selected from hydrogen, (1-4C)alkyl, (1-4C)alkoxy, (1-2C)alkoxy(1-2C)alkyl, fluorine, CF₃, (2-4C)alkanoyl, (1-2C)alkoxycarbonyl, fluoro(-1-4C)alkoxy, hydroxy(1-4C)alkyl, or wherein R² and R³ form a group —OCH₂O, —OCF₂O, —OCF₂—CHFO—, or —C(CH₃)₂COC(CH₃)₂—.

5. Compounds wherein R¹, R², R³ and R⁴ are the same or different and selected from hydrogen, methyl, ethyl, isopropyl, t-butyl, methoxy, ethoxy, methoxymethyl, ethoxymethyl, fluorine, trifluoromethoxy, tetrafluoroethoxy, hydroxymethyl, or wherein R² and R³ form a group —OCF₂O—, —C(CH₃)₂COC(CH₃)₂—, or —OCH₂O—.

6. Compounds wherein R¹, R², R³ and R⁴ are the same or different and selected from hydrogen, t-butyl, methoxy, ethoxy, methoxymethyl, ethoxymethyl, fluorine, trifluoromethoxy, tetrafluoroethoxy, hydroxymethyl or hydroxyethyl.

7. Compounds wherein R¹ and R⁴ are H and R² and R³ are selected from t-butyl, methoxy, methoxymethyl, fluorine, trifluoromethoxy, hydroxymethyl and hydroxyethyl.

8. Compounds wherein R¹, R², R³ and R⁴ are H, alkyl containing 1-6 carbon atoms, or alkoxy containing 1-6 carbon atoms.

9. Compounds wherein R¹ and R⁴ are H and R² and R³ both are alkoxy containing 1-3 carbon atoms.

10. Compounds wherein R¹, R², R³ and R⁴ all are H.

11. Compounds wherein R¹ and R⁴ are alkoxy containing 1-3 carbon atoms and R² and R³ are H or hydroxyalkyl containing 1-3 carbon atoms.

12. Compounds wherein R¹, R³ and R⁴ are H and R² is OCH₃.

13. Compounds wherein R¹, R² and R⁴ are H and R³ is OCH₃.

14. Compounds wherein R⁷ is H, alkyl containing 1-6 carbon atoms, alkoxy containing 1-6 carbon atoms.

15. Compounds wherein R⁷ is aryloxy or arylalkoxy, optionally substituted.

16. Compounds wherein R⁷ is alkoxy containing 1-6 carbon atoms.

17. Compounds wherein R⁹ is H or CH₃, especially H.

18. Preferred substituents in position 1 of the benzimidazole nucleus are those where R⁹ is H and D is as exemplified in Table 1 below.

19. Compounds wherein D is

20. Compounds wherein D is

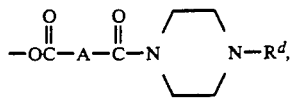

particularly acid addition salts thereof.

21. Compounds wherein D is

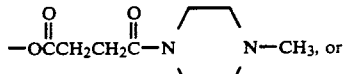

22. Compounds wherein D is

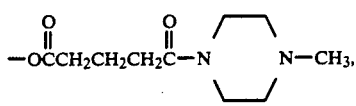

particularly acid addition salts thereof.

22. Compounds wherein D is

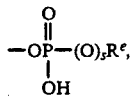

particularly alkali salts thereof.

23. Compounds wherein D is

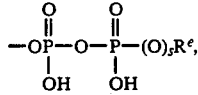

particularly alkali salts thereof.

24. Compounds wherein D is

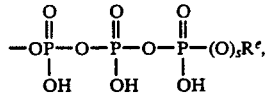

particularly alkali salts thereof.

25. Compounds wherein D is

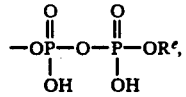

particularly alkali salts thereof.

26. Compounds wherein D is

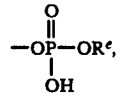

particularly alkali salts thereof.

27. Compounds wherein D is

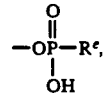

particularly alkali salts thereof.

28. Compounds wherein D is

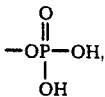

particularly alkali salts thereof.

29. Compounds wherein D is

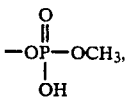

particularly alkali salts thereof.

30. Compounds wherein D is

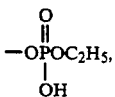

particularly alkali salts thereof.

31. Compounds wherein $R^e$ is an optionally substituted aryl group.

32. Preferred benzimidazole structures are: unsubstituted, 5-methoxy and 6-methoxy-substituted.

33. Preferred of the pyridine fragments are: 3,5-dimethyl-4-methoxy-, 3-methyl-4-methoxy-, 5-ethyl-4-methoxy-, 4-methoxy-, 4-ethoxy-, 4-isopropoxy-, 3,5-dimethyl-, 3,4-dimethyl-, 4,5-dimethyl-, 3-methyl-4-(2,2,2-trifluoro)ethoxy-, 3,4-dimethoxy, 4,5-dimethoxy-, 3-methyl-4-ethylthio-, 3-methyl-4,5-dimethoxy, 3,4,5-trimethyl, 3-ethyl-4-methoxy-, 3-n-propyl-4-methoxy-, 3-isopropyl-4-methoxy-, 3-t-butyl-4-methoxy-substituted.

34. Particularly preferred of the pyridine fragments are: 3,5-dimethyl-4-methoxy-, 3-methyl-4-methoxy, 3-ethyl-4-methoxy, 3-isopropyl-4-methoxy, 4-methoxy, 4-ethoxy- and 4-isopropoxy-substituted, especially 3,5-dimethyl-4-methoxy-substituted.

35. Additional preferred compounds are obtained by combining the indicated preferred meanings for some or all of the radicals X and $R^1$-$R^{10}$ as indicated in the groups 1-34 above.

36. Preferred of the pyridinylmethylsulfinyl benzimidazole moieties are

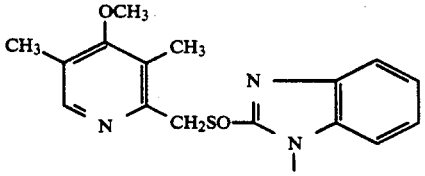

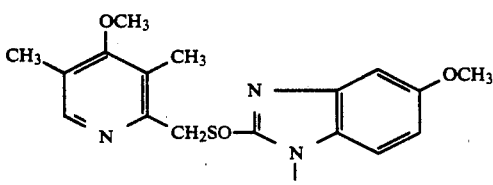

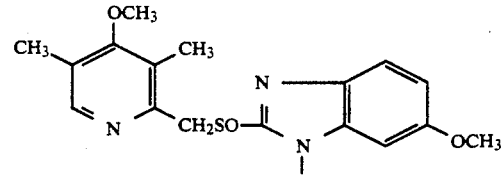

37. Preferred groups of the radicals $R^6$ and $R^8$ are H, $CH_3$, $C_2H_5$, n-$C_3H_7$, i-$C_3H_7$, and t-$C_4H_9$.

38. The most preferred compounds of the invention are

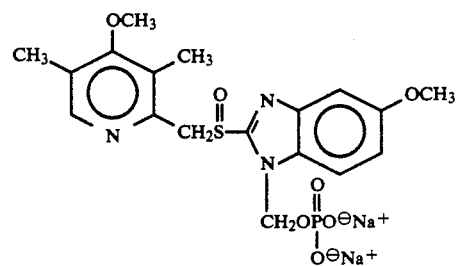

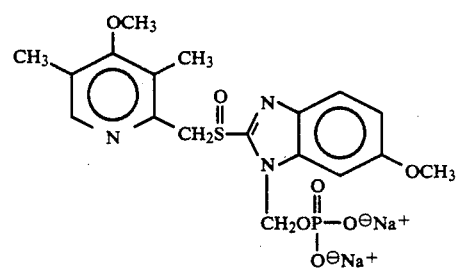

39. Other preferred compounds of the invention are

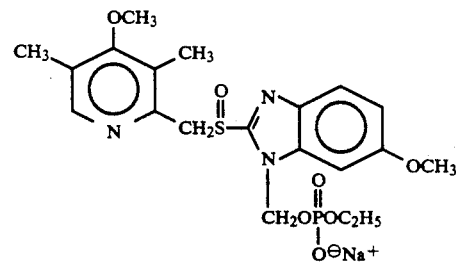

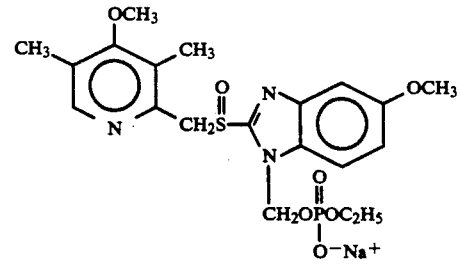

Illustrative examples of the various radicals in the formula I are as follows. These illustrative examples will be applicable to the different radicals depending on the number of carbon atoms prescribed for each radical.

The group alkyl in the definitions of $R^1$, $R^2$, $R^3$, $R^4$, $R^5$, $R^6$, $R^7$, $R^8$ $R^9$, $R^{10}$, $R^a$, $R^b$, $R^c$, $R^d$, $R^e$ and $R^g$ are exemplified by methyl, ethyl, n-propyl, isopropyl, n- butyl, isobutyl, t-butyl, n-pentyl, n-hexyl, cyclopropyl, cyclopentyl, cyclohexyl, cyclopropylmethyl, cyclopentylmethyl, cyclopentylethyl, and cyclohexylmethyl. Lower alkyl groups containing 1–4 carbon atoms are especially preferred.

The group alkoxy in the definitions of $R^1$, $R^2$, $R^3$, $R^4$, $R^6$, $R^7$, $R^8$ and $R^{10}$ are exemplified by methoxy, ethoxy, n-propoxy, iso-propoxy, n-butoxy, i-butoxy, s-butoxy, t-butoxy, n-pentoxy, i-pentoxy, n-hexoxy, cyclopropoxy, cyclopentoxy, cyclohexoxy, cyclopropylmethoxy, cyclopentylmethoxy, cyclopentylethoxy, and cyclohexylmethoxy. Lower alkoxy groups are preferred, especially those containing 1–4 carbon atoms, preferably a lower alkoxy group having especially preferred 1–3 carbon atoms, e.g. methoxy, ethoxy, n-propoxy or isopropoxy.

Halogen in the definitions of $R^1$, $R^2$, $R^3$, $R^4$, $R^6$ and $R^8$ is chloro, bromo, fluoro and iodo, preferably chloro, bromo, and fluoro.

In $R^1$, $R^2$, $R^3$, $R^4$ and $R^7$ when representing alkylthio or alkylsulfinyl is the alkyl preferably a lower alkyl having especially preferred 1–4 carbon atoms, e.g. methylthio, methylsulfinyl, ethylthio, ethylsulfinyl, isopropylthio, n-butylsulfinyl or isobutylthio.

The group aryl when present in $R^1$, $R^2$, $R^3$, $R^4$, $R^7$, $R^{10}$ and $R^e$ has preferably up to 10 carbon atoms, especially preferred up to 6 carbon atoms, e.g. a phenyl group.

$R^1$, $R^2$, $R^3$, $R^4$, and $R^7$ representing an aryloxy or arylthio group have preferably up to 10 carbon atoms, especially preferred up to 6 carbon atoms, e.g. a phenoxy or phenylthio group.

The groups arylalkyl, arylalkoxy, and arylalkylthio, when present in $R^1$, $R^2$, $R^3$, $R^4$, $R^7$, $R^8$ and $R^e$ have preferably up to 10 carbon atoms in the aryl group. Especially preferred are 6 carbon atoms in the aryl group and 1–3 carbon atoms in the alkyl group or alkoxy group, respectively, e.g. phenylmethyl, phenylethyl, phenylmethoxy, phenylethoxy, phenylpropyl, phenylisopropoxy, phenylmethylthio, and phenylethylthio.

The group "(4–9C)alkylen containing a cycloalkylene group" when present in A is especially

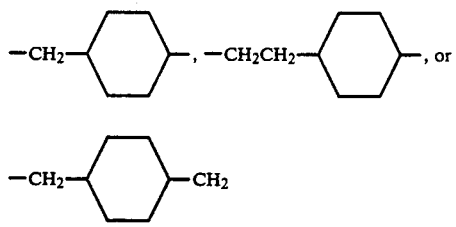

$R^1$, $R^2$, $R^3$, $R^4$ and $R^7$ representing an alkoxy alkyl or alkoxyalkoxy group are exemplified by methoxymethyl, methoxyethyl, methoxypropyl, ethoxymethyl, ethoxyethyl, propoxyethyl, methoxymethoxy, methoxyethoxy, methoxypropoxy, ethoxyethoxy and propoxyethoxy.

$R^7$ representing an alkenyloxy or alkynyloxy group has preferably 2–7 carbon atoms, especially preferred 3–4 carbon atoms, e.g. allyloxy, propargyloxy, 2-butenyloxy and 2-butynyloxy.

Illustrative examples of ring structures formed by $R^1$ and $R^2$, $R^2$ and $R^3$ and $R^3$ and $R^4$ are —$CH_2CH_2CH_2$—, —$CH_2CH_2CH_2CH_2$—, —$CH_2C(CH_3)_2CH_2$—, —$(CH_2)_5$—, —$CH=CH—CH=CH$—, —$CH_2COCH_2$—, —$OCH_2O$—, —$OCH_2CH_2O$—, —$OCH_2CH_2CH_2O$—, —$OCH_2CH_2$—, —$CH_2CH_2NH$—, —$CH=CH—CH=N$—, —$COCH_2CO$—, —$SCH_2CH_2$—, —$SCH_2S$—, —$SCH_2CH_2S$—, —$C(CH_3)_2—CO—C(CH_3)_2$—, —$OCF_2O$—, —$OCF_2CHFO$—, —$OCF_2CF_2O$—, and —$OCF_2CFClO$—.

$R^6$ and $R^7$, or $R^7$ and $R^8$ representing a 5- or 6-membered saturated or unsaturated ring is preferably a saturated carbocyclic ring or a saturated ring containing an oxygen or a sulphur atom in the 4-position in the pyridine ring, e.g. —$CH_2CH_2CH_2$—, —$CH_2CH_2CH_2CH_2$—, —$O—CH_2CH_2$—, —$O—CH_2CH_2CH_2$—, —$SCH_2CH_2$—, or $SCH_2CH_2CH_2$—.

$R^1$, $R^2$, $R^3$ and $R^4$ when representing haloalkoxy is preferably a lower haloalkoxy. Especially preferred are lower fluoroalkoxy, or fluorochloroalkoxy groups, e.g. $OCF_3$, $OCHF_2$, $OCF_2CHF_2$, $OCF_2CF_3$, $OCF_2Cl$, $OCH_2CF_3$.

$R^7$ when representing fluoroalkoxy is exemplified by $OCH_2CF_3$, $OCH_2CF_2CF_3$ and $OCH_2CF_2CHF_2$.

$R^1$, $R^2$, $R^3$ and $R^4$ representing hydroxyalkyl is exemplified by $CH_2OH$, $CH_2CH_2OH$, $CH_2CH_2CH_2OH$, and $(CH_2)_4OH$.

$R^7$ when representing a dialkylamino group is preferably —$N(CH_3)_2$, or —$N(C_2H_5)_2$.

$R^f$, which represents the side chain of an amino acid is e.g. $CH_3$ derived from alanine or $(CH_2)_2COOH$ derived from glutamic acid.

For the compounds with the general formula I containing an asymmetric centre, both the pure enantiomers and the racemic mixtures are within the scope of the present invention.

Further illustrative examples of the radicals in the formula I are given in the examples and lists of specific compounds given elsewhere in this specification.

It is believed that compounds of formula I are metabolized before exerting their effect. Such metabolism may occur in the N-substituent in position 1 in the benzimidazole nucleus. Moreover, compounds of the invention wherein X is S are believed to exert their antisecretory activity after metabolism to compounds wherein X is SO.

Preparation

The compound of the formula I wherein D is $R^5COO$ may be prepared by

A. Reacting a compound of the formula II

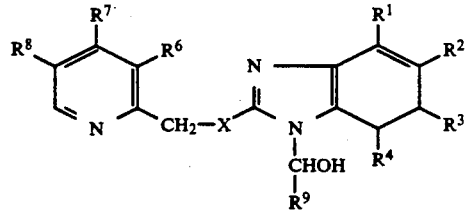

where $R^1$, $R^2$, $R^3$, $R^4$, $R^5$, $R^6$, $R^7$, $R^8$, $R^9$ and X are as defined under formula I with a compound of the formula III $R^5COOH$  III or an activated derivative thereof, wherein $R^5$ is as defined under formula I above.

The reaction of a compound of formula II with a compound of formula III is suitably carried out either directly in the presence of dicyclohexylcarbodiimide and if desired also in the presence of N,N-dimethylaminopyridine (DMAP) or with an activated form of compound III, such as an acid halide or a mixed anhydride or a carbonate.

Suitable solvents are hydrocarbons such as toluene and benzene or halogenated hydrocarbons such as methylen chloride and chloroform or polar solvents such as acetone, dimethyl formamide (DMF), acetonitrile tetrahydrofuran (THF) and pyridine.

The reaction of the compounds of formulas II and III may be carried out at a temperature between $-15°$ C. and the boiling temperature of the reaction mixture.

B. For the preparation of compounds of the formula I wherein $R^9$ is H, reacting a compound of the formula IV

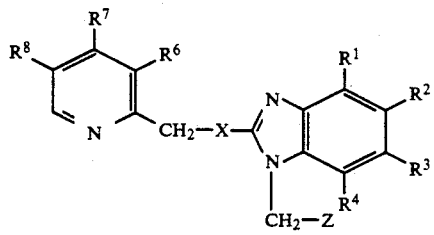
IV wherein $R^1$, $R^2$, $R^3$, $R^4$, $R^6$, $R^7$, $R^8$ and X are as defined under formula I, and Z is halogen such as Cl, Br or I or a functionally equivalent group, with a compound of the formula V, VI, VII, VIII, IX, X, XI, XII, or XIII:

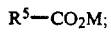 V

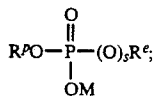 VI

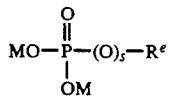 VII

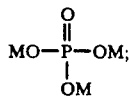 VIII

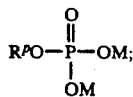 IX

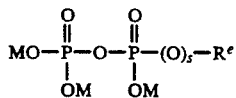 X

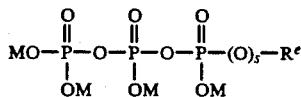 XI

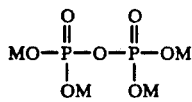 XII

-continued

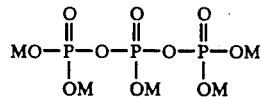 XIII wherein s, $R^5$, and $R^e$ are as defined under formula I above, $R^p$ is a suitable protecting group such as cyanoethyl, benzyl or p-nitrophenyl, and M is a counter ion such as Na+, K+, Ag+ or trialkylammonium. In the case where a protecting group is used, such protecting group is removed after the coupling reaction (see under E below).

C. Oxidizing a compound of the formula I

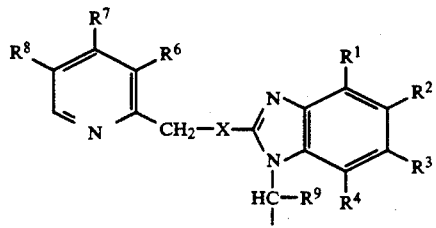 I wherein X is S, $R^1$, $R^2$, $R^3$, $R^4$, $R^6$, $R^7$, $R^8$, $R^9$ and D have the meanings given, to give a compound of the same formula I wherein X is SO. This oxidation may be carried out by using an oxidating agent selected from the group consisting of nitric acid, hydrogen peroxide, peracids, peresters, ozone, dinitrogentetraoxide, iodosobenzene, N-halosuccinimide, 1-chlorobenzotriazole, t-butylhypochlorite, diazabicyclo-|2,2,2|-octane bromine complex, sodium metaperiodate, selenium dioxide, manganese dioxide, chromic acid, cericammonium nitrate, bromine, chlorine, and sulfuryl chloride. The oxidation usually takes place in a solvent wherein the oxidizing agent is present in some excess in relation to the product to be oxidized.

The oxidation may also be carried out enzymatically by using an oxidating enzyme or microbiotically by using a suitable microorganism.

D. Reacting a compound of the formula IIA

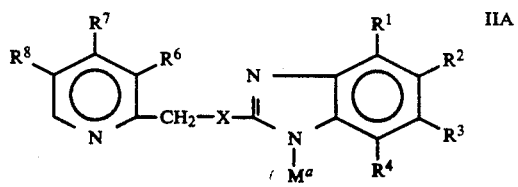 IIA wherein $R^1$, $R^2$, $R^3$, $R^4$, $R^6$, $R^7$, $R^8$ and X are as defined under formula I and $M^a$ is either a metal cation such as Na+, K+, Li+ or Ag+ or a quaternary ammonium ion, such as tetrabutylammonium with a compound of the formula

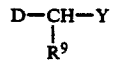 XII wherein D and $R^9$ are as defined under formula I and Y is halogen such as Cl, Br or I, or a functionally equivalent group.

The reaction of a compound of formula IIA with a compound of formula XII is suitably carried out under protective gas in absence of water. Suitable solvents are hydrocarbons such as toluene and benzene and halogenated hydrocarbons such as methylene chloride and chloroform.

The reaction of the compounds of formula IIA and XII may be carried out at a temperature between the ambient temperature and the boiling temperature of the reaction mixture.

E. Removal of a protective group in the D substituent is done by methods well known in the art. Thus, for instance, the phosphates may be protected as dibenzyl- or diphenyl esters, which can be cleaved by basic hydrolysis. The dibenzyl esters may also be cleaved by sodium iodide in acetone. The cyanoethyl protecting group may be removed by treatment with a base such as NaOH.

Depending on the process conditions and the starting materials, the end products of the formula I are obtained either in neutral or salt form. Both the neutral compounds and the salts of these end products are included within the scope of the invention. Thus, salts may be obtained as well as hemi, mono, sesqui or polyhydrates.

Acid addition salts of the amino-containing compounds may in a manner known per se be transformed into free base using basic agents such as alkali or by ion exchange. The free bases obtained may then be converted into salts with organic or inorganic acids. In the preparation of acid addition salts preferably such acids are used which form suitable therapeutically acceptable salts. Examples of such acids are hydrohalogen acids, sulfonic acid, phosphoric acid, nitric acid, and perchloric acid; aliphatic, alicyclic, aromatic or heterocyclic carboxyl or sulfonic acids, such as formic acid, acetic acid, propionic acid, succinic acid, glycolic acid, lactic acid, malic acid, tartaric acid, citric acid, ascorbic acid, maleic acid, hydroxymaleic acid, pyruvic acid, phenylacetic acid, benzoic acid, p-aminobenzoic acid, p-hydroxybenzoic acid, salicylic acid or p-aminosalicylic acid, embonic acid, methanesulfonic acid, ethanesulfonic acid, hydroxyethanesulfonic acid, ethylenesulfonic acid, halogenbenzenesulfonic acid, toluenesulfonic acid, napthylsulfonic acid or sulfanilic acids, methionine, tryptophane, lysine or arginine.

Base addition salts of the carboxylic acid—or phosphorous—containing compounds may in a corresponding way be transformed into the acid form, and then reconverted to a therapeutically suitable salt such as sodium and potassium salts.

Racemates obtained can be separated according to known methods, e.g. recrystallization from an optically active solvent.

In the case of diastereomeric mixtures (racemate mixtures) these may be separated into stereoisomeric (diastereomeric) pure racemates by means of chromatography or fractional crystallization.

The starting materials utilized in the methods A-E are in some cases novel. These novel starting materials may, however, be obtained according to processes known per se.

Starting materials of the formula II are obtained by reaction of the corresponding benzimidazole compound carrying H in the N-1 position with an aldehyde $R^9CHO$.

Starting materials of the formula IV are novel and constitute as such part of the invention. Compounds of the formula IV wherein Z is Cl are prepared by reaction of a compound of the formula II with a chlorinating agent such as $SOCl_2$ in the presence of a suitable base such as triethylamine in a suitable solvent such as $CH_2Cl_2$, toluene, acetonitrile, tetrahydrofuran or mixtures thereof. For the preparation of compounds of the formula IV wherein Z is Br or I, analogous methods are used utilizing suitable reagents containing bromine, such as $BBr_3$, or iodine. Examples of these intermediates are given in Example 11 to 139 in Table 3 below.

The starting materials having X=S, utilized in Method C may be obtained according to Method A, or Method B.

In a further aspect, the invention relates to the use, as means for increasing the aqueous solubility of gastric acid-inhibiting benzimidazole derivatives, of a radical of the formula

where D and $R^9$ are as defined in formula I, as substituent in position N-1 of the benzimidazole nucleus.

The invention also relates to gastric acid-inhibiting benzimidazole derivatives having in position N-1 of the benzimidazole nucleus a radical of the formula $D-CH(R^9)-$, where D and $R^9$ are as defined in formula I.

The preferred meanings of D and $R^9$ are as stated elsewhere in this specification.

The invention also relates to the use as agent to be linked to position N-1 of the benzimidazole nucleus, for increasing the aqueous solubility of benzimidazole derivatives having gastric acid inhibiting effect, of a compound of the formula

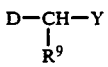

where D, $R^9$ and Y are as defined elsewhere in this specification.

For clinical use the compounds of the invention are formulated into pharmaceutical formulations for oral, rectal, parenteral or other mode of administration. It is especially preferred to formulate the compounds of the invention into pharmaceutical formulations for parenteral administration. The pharmaceutical formulation contains a compound of the invention in combination with a pharmaceutically acceptable carrier. The carrier may be in the form of a solid, semi-solid or liquid diluent, or a capsule. These pharmaceutical preparations are a further object of the invention. Usually the amount of active compounds is between 0.1-95% by weight of the preparation, between 0.2-20% by weight in preparations for parenteral use and between 1 and 50% by weight in preparations for oral administration.

In the preparation of pharmaceutical formulations containing a compound of the present invention in the form of dosage units for oral administration the compound selected may be mixed with a solid, powdered carrier, such as lactose, saccharose, sorbitol, mannitol, starch, amylopectin, cellulose derivatives, gelatin, or another suitable carrier, as well as with lubricating agents such as magnesium stearate, calcium stearate, sodium stearyl fumarate and polyethylenglycol waxes. The mixture is then processed into granules or pressed into tablets. Granules and tablets containing sulfoxides may be coated with an enteric coating which protects the active compound from acid catalyzed degradation as long as the dosage form remains in the stomach. The enteric coating is chosen among pharmaceutically acceptable enteric-coating materials e.g. beeswax, shellac or anionic film-forming polymers such as cellulose acetate phthalate, hydroxypropyl-methylcellulose phthalate, partly methyl esterified methacrylic acid polymers and the like, if preferred in combination with a suitable plasticizer. To this coating various dyes may be added in order to distinguish among tablets or granules with different active compounds or with different amounts of the active compound present.

soft gelatine capsules may be prepared with capsules containing a mixture of the active compound or compounds of the invention, vegetable oil, fat, or other suitable vehicle for soft gelatine capsules. Soft gelatine capsules may also be enteric-coated as described above. Hard gelatine capsules may contain granules or enteric-coated granules of the active compound. Hard gelatine capsules may also contain the active compound in combination with a solid powdered carrier such as lactose, saccharose, sorbitol, mannitol, potato starch, amylopectin, cellulose derivatives or gelatine. The hard gelatine capsules may be enteric-coated as described above.

Dosage units for rectal administration may be prepared in the form of suppositories which contain the active substance mixed with a neutral fat base, or they may be prepared in the form of a gelatine rectal capsule which contains the active substance in a mixture with a vegetable oil, paraffin oil or other suitable vehicle for gelatine rectal capsules, or they may be prepared in the form of a ready-made micro enema, or they may be prepared in the form of a dry micro enema formulation to be reconstituted in a suitable solvent just prior to administration.

Liquid preparation for oral administration may be prepared in the form of syrups or suspensions, e.g. solutions or suspensions containing from 0.2% to 20% by weight of the active ingredient and the remainder consisting of sugar or sugar alcohols and a mixture of ethanol, water, glycerol, propylene glycol and polyethylene glycol. If desired, such liquid preparations may contain colouring agents, flavouring agents, saccharine and carboxymethyl cellulose or other thickening agents. Liquid preparations for oral administration may also be prepared in the form of a dry powder to be reconstituted with a suitable solvent prior to use.

Solutions for parenteral administration may be prepared as a solution of a compound of invention in a pharmaceutically acceptable solvent, preferably in a concentration from 0.1% to 10% by weight. These solutions may also contain stabilizing agents and/or buffering agents and may be manufactured in different unit dose ampoules or vials. Solutions for parenteral administration may also be prepared as a dry preparation to be reconstituted with a suitable solvent extemporaneously before use.

The typical daily dose of the active substance varies within a wide range and will depend on various factors such as for example the individual requirement of each patient, the route of administration and the disease. In general, oral and parenteral dosages will be in the range of 5 to 500 mg per day of active substance.

The invention is illustrated by the following examples.

EXAMPLE 1

Preparation of 1-Methylpiperidine-4-yl carboxylic acid, [2[[(4-methoxy-3,5-dimethyl-2-pyridinyl) methyl] sulfinyl]-1H-benzimidazole-1-yl] methyl ester. Hydrogen bromide salt (Method A)

To a stirred mixture of 4-carboxy-N-methyl piperidine (1.8 g 0.01 mol) in acetone (75 ml) triethylamine (1.5 g 0.015 mol) and iso butyl chloroformiate (1.93 ml 0.015 mol) was added. the mixture was stirred for 15 min. at room temperature. [2-[[(4-methoxy-3,5-dimethyl-2-pyridinyl methyl]sulfinyl]-1H-benzimidazole-1-yl]methanol (0.01 mol) dissolved in pyridine (15 ml) was added dropwise. After the addition, the mixture was stirred for 2 hr at room temperature. The inorganic salts were removed by filtration. The filtrate was evaporated and the residue was dissolved in dichloromethane (100 ml). The dichloromethane solution was washed 3 times with 0,5M NaOH solution (10 ml) and then once with water (25 ml). Drying of the organic phase, filtration and evaporation of the solvent gave the title compound. Yield: 0,4 g (8,5%). The hydrogen bromide salt (title compound) was prepared from the free base by conventional methods.

EXAMPLE 2

Preparation of p-N,N-Dimethylaminomethylbenzoic acid, [2-[[(4-methoxy-3,5-dimethyl-2-pyridinyl)methyl]sulfinyl]-1H-benzimidazole-1-yl] methyl ester (Method B)

p-N,N-Dimethylaminomethylbenzoic acid (50 mg, 0.28 mmoles) and triethyl amine (60 mg, 0.6 mmoles) were dissolved in methylene chloride (10 ml).

A solution of 1-chloromethyl-2-[[(4-methoxy-3,5-dimethyl-2-pyridinyl) methyl]sulfinyl]-1H-benzimidazole (100 mg, 0,27 mmoles) in methylene chloride (5 ml) was added. After 10 hr at room temperature the methylene chloride solution was washed with 0,5M sodium hydroxide (5 ml) and brine (5 ml). The organic phase was dried over sodium sulphate, filtered and evaporated at a reduced pressure. The residue is the essentially pure title compound. Yield: 56 mg (40%).

EXAMPLE 3

The compound of this example is identified in Table 1, and was prepared by Method A as exemplified in Example 1.

EXAMPLE 10

Preparation of Phosphoric acid, benzyl-[2[[(4-methoxy-3,5-dimethyl-2-pyridinyl)methyl]sulfinyl]-1H-benzimidazole-1-yl]methyl diester, sodium salt (Method E)

Phosphoric acid, dibenzyl-[2-[[(4-methoxy-3,5-dimethyl-2-pyridinyl) methyl]sulfinyl]-1H-benzimidazole-1-yl]methyl triester (90 mg, 0.15 mmoles) was dissolved in methanol/water (2 ml, 1:1). Sodium hydrogen carbonate (58 mg, 0,7 mmoles) was added and the mixture was refluxed for 2 hours on a waterbath. Concentration of the mixture at reduced pressure and chromatography of the residue on silica gel (ethyl acetate-methanol-water; 20:4:3) gave the essentially pure title compound. Yield: 30 mg (37%).

EXAMPLES 12, 13, 15 AND 16

These compounds are identified in Table 1 and were prepared by Method A as exemplified in Example 14.

EXAMPLE 14

Preparation of
2-[[(4-Methoxy-3,5-dimethyl-2-pyridinyl)methyl]sulfinyl]-1H-benzimidazole-1-yl]methyl(1-methyl-4-piperidinyl)carbonate. Hydrogen bromide salt (Method A)

p-Nitrophenyl chloroformiate (3.1 g 15 mmoles) was dissolved in toluene (75 m). A solution of 4-Hydroxy-1-methylpiperidine (1.75 g, 15 mmoles) and triethyl amine in toluene (75 ml) was added with stirring (5 min) at room temperature. After 5 min at room temperature the reaction mixture was filtered and the filtrate was evaporated at a reduced pressure. The oily residue was taken up in methylene chloride (50 ml) and added to a solution of 2-[[(4-methoxy-3,5-dimethyl-2-pyridinyl)methyl]-sulfinyl-1H-benzimidazole-1-yl]methanol (10 mmoles) and triethyl amine (1 g, 10 mmoles) in methylene chloride (50 ml). The methylene chloride was distilled off and the residue was heated on a water bath for 5 minutes at 70° C. After cooling to room temperature methylene chloride (100 ml) was added and the solution was extracted with sodium hydroxide (1M, 16 ml), washed with brine and dried over anhydrous sodium sulphate. Filtration and evaporation of the solvent from the filtrate gave an oil residue, from which the free base of the title compound crystallized by addition of a ethyl acetate-diethylether mixture. Yield: 1.4 g. Mp 134°–136° C.

NMR (500 MHz, CDCl$_3$, δ) 2.22, 2.25, 2.30, 3.70, 4.96, 6.52, 7.40, 7.74, 8.14.

The hydrogen bromide salt (title compound) was prepared from the free base by conventional methods.

EXAMPLE 23

Preparation of
1,1-Dimethyl-4-[2[[(4-methoxy-3,5-dimethyl-2-pyridinyl)methyl]sulfinyl]-1H-benzimidazole-1-yl]methoxy carbonyloxypropyl piperazinium iodide The title compound is prepared by alkylation of 2-[[(4-Methoxy-3,5-dinethyl-2-pyridinyl)methyl]sulfinyl]-1H-benzimidazole-1-yl]methyl-3-(1-methyl piperzine-4-yl)propyl carbonate with methyl iodide by conventional methods.

EXAMPLES 29 and 32 a) Preparation of mixture of phosphoric acid, [6-methoxy-[2-[[(4-methoxy-3,5-dimethyl-2-pyridinyl)-methyl]sulfinyl]-1H-benzimidazole-1-yl]]methyl ester, di-sodium salt and phosphoric acid, [5-methoxy-[2-]4-methoxy-3,5-dimethyl-2-pyridinyl)-methyl]sulfinyl]-1H-benzimidazole-1-yl]]methyl ester, disodium salt, 2:1 (Method B)

Tributylamine (14 ml, 0.059 mol) was added with stirring to a solution of phosphoric acid, 85 percent (2 ml, 0.030 mol) in ethanol (10 ml). The solvent was evaporated and the residue taken up in methylene chloride (25 ml). The organic phase was dried over sodium sulphate, filterered and evaporated. A mixture of 1-chloromethyl-6-methoxy-2 ]](4-methoxy-3,5-dimethyl-2-pyridinyl)methyl]sulfinyl]-1H-benzimidazole and 1-chloromethyl-5-methoxy-2[[(4-methoxy-3,5-dimethyl-2-pyridinyl)methyl]sulfinyl]-1H-benzimidazole, 2:1 (1.0 g, 0.0025 mol) and the tributylammonium salt of phosphoric acid, prepared above, were dissolved in methylene chloride (50 ml). The methylene chloride was distilled off and the residue was heated on a waterbath for 5 minutes at 60° C. The residue was dissolved in methylene chloride (50 ml) and again the methylene chloride was distilled off and the oily product mixture was heated on a waterbath for 5 minutes at 60° C. This procedure was repeated four times until the reaction was completed. The residue was dissolved in methylene chloride and washed with three portions of water. The organic layer was dried, filtered and evaporated. The crude mixture of tributylammonium salts was dissolved in methylene chloride (25 ml) and water (10 ml) added. A solution of sodium hydroxide was added with stirring while pH of the aqueous layer was carefully controlled. When pH reached 9.0–9.5 in the aqueous phase (0.005 mol NaOH added) the mixture was centrifuged. The aqueous layer was washed with three portions (25 ml) of methylene chloride and then freeze dried to give 760 mg, 61% of the title compounds. NMR spectrum of the mixture was in accordance with the spectra of the pure isomers given in Table 2.

b) Preparation of Phosphoric acid, [5-methoxy-[2[[(4-methoxy-3,5-dimethyl-2-pyridinyl) methyl]sulfinyl]-1H-benzimidazole-1-yl]]methyl ester, disodium salt From the mixture of tributyl, ammonium salts prepared in step a) above phosphoric acid, [5-methoxy-[2[[(4-methoxy-3,5-dimethyl-2-pyridinyl) methyl]sulfinyl]-1H-benzimidazole-1-yl]methyl ester, tributylammonium salt was obtained through chromatography on a reversed phase column, eluted with 15 percent acetonitrile in water. After freeze drying the compound was dissolved in methylene chloride acid treated with sodiumhydroxide as described above. Pure phosphoric acid, [5-methoxy-[2[[(4-methoxy-3,5-dimethyl-2-pyridinyl)-methyl]sulfinyl]-1-H-benzimidazole-1-yl]]methyl ester, disodium salt was obtained in about 1% yield. NMR spectrum in Table 2.

c) Preparation of Phosphoric acid, [6-methoxy-[2-[[(4-methoxy-3,5-dimethyl-2-pyridinyl)-methyl]sulfinyl]-1H-benzimidazole-1yl]]methyl ester, di-sodium salt

Method B

The title compound was prepared as described in step a) above for the isomeric mixture, starting from pure 1-chloromethyl-6-methoxy-2[[(4-methoxy 3,5-dimethyl-2-pyridinyl)methyl]sulfinyl]-1H-benzimidazole (1.9 g, 0.0048 mol), phosphoric acid, 85 percent (4 ml, 0.060 mol), tributyl amine (28 ml, 0.118 mol) and 100 ml methylene chloride. The product was crystallized from an ethanol-water mixture giving 0.85 g, 35 h. NMR spectrum of the compound was identical with the spectrum given in Table 2.

Method E

To the residue from the preparation of Phosphoric acid, cyanoethyl-6-methoxy-[2-[(4-methoxy-3,5-dimethyl-2-pyridinyl)methyl]sulfinyl]-1H-benzimidazole-1-yl]methyl diester, triethylammonium salt was added a solution of NaOH (0.30 g, 0.0075 mol) dissolved in water (25 ml). After heating the mixture on a waterbath (60° C.) for 15 minutes it was washed twice with methylene chloride (25 ml) and evaporated to dryness, giving the desired compound (0.25 g). The identity of the product was confirmed with NMR. Yield 22%.

Example 33

Preparation of Phosphoric acid,
ethyl-[6-methoxy-[2-[(4-methoxy-3,5-dimethyl-2-pyridinyl)methyl]sulfinyl] 1H-benzimidazole-1-yl] methyldiester, sodium salt Pure 1-chloromethyl-6-methoxy-2[[(4-methoxy-3,5-dimethyl-2-pyridinyl)methyl]sulfinyl]1H-benzimidazole (0.3 g, 0.00076 mol) and the mono-triethylammonium salt of phosphoric acid mono ethyl ester (0.5 g, 0.0022 mol) were mixed together with triethyl amine (0.3 ml) and methylene chloride (10 ml). The solvent was evaporated and the residue was heated on a water bath at 60° C. for 5 minutes. Methylene chloride was added, distilled off and the product was again heated for 5 minutes at 60° C. This procedure was repeated four times until the reaction was completed. The crude material was purified by chromatography on a reversed phase column with water-acetonitrile 90:10 as eluent. The pure fractions were combined, evaporated and one equivalent of sodium hydroxide was added. The solution was evaporated and dried in vacuum, yielding 0.37 g, 26% of pure product. The title compound was identified with NMR.

EXAMPLES 34 AND 35

Preparation of a mixture of 1-piperazinebutanoic acid, 4-methyl-γ-oxo-,
[5-methoxy-2-[[(4-methoxy-3,5-dimethyl-2-pyridinyl)-methyl] sulfinyl]-1H-benzimidazole-1-yl]methyl ester and 1-piperazine butanoic acid, 4-methyl-1-γ-oxo, [6-methoxy-2-[[(4-methoxy-3,5-dimethyl-2-pyridinyl)-methyl]sulfinyl-1H-benzimidazole-1-yl]methyl ester 1:2
(Method A)

Butandioic acid anhydride (4 g 0.04 mol), N-methyl piperazine (4 g 0.04 mol) and triethylamine (4 g 0.04 mol) was added to dichloromethane (250 ml). The mixture was stirred for 10 min. at room temperature. The mixture was cooled to −15° C. and methylchloroformate (3.78 g 0.04 mol) was added. The isomeric mixture of 1-hydroxymethyl-(5-methoxy)-and-(6-methoxy)-2-[[(4-methoxy-3,5-dimethyl-2-pyridinyl)methyl]sulfinyl]-1H-benzimidazole (15 g 0.04 mol) and triethylamine (4 g 0.04 mol) was dissolved in dichloromethane (75 ml) and then added drop wise to the mixed anhydride solution. Dimethylaminopyridine (0.49 g 0.04 mol) was then added and the temperature was risen and the mixture stirred at room temperature for 90 minutes. The solution was washed twices with water (150 ml) and then twice with sodiumhydroxide (50 ml 0.5M) the phases were separated and the dichloromethane was dried, filtrated and evaporated giving the title products. Yield 15.2 g. The residue was crystallized in a mixture of diethylether (80 ml) and ethylacetate (80 ml) yielding 12.2 g, 56% of the title compounds as an isomeric mixture in the ratio 1:2.

EXAMPLE 45

Preparation of Phosphoric acid,
p-nitrophenyl-[2[[(4-methoxy-3,5-dimethyl-2-pyridinyl)methyl]sulfinyl]-1H-benzimidazole-1-yl]methyl diester, sodium salt 1-Chloromethyl-2-[[(4-methoxy-3,5-dimethyl-2-pyridinyl)methyl]sulfinyl]-1H-benzimidazole (0.22 g, 0.60 mmol), disodium-p-nitrophenylphosphate x 6H$_2$O (2.4 g, 6.4 mmol) were dissolved in 15 ml of acetonitrile containing 10 ml of water. The solution was refluxed for 1 hour. The solvents were then removed in vacuum and the residue dissolved in water. The aqueous layer was washed with methylene chloride and then evaporated. The crude material was purified by flash chromatography on silica with ethylacetate-methanol-water (20:4:3) as eluent, giving 32 mg (10%) of pure title compound.

EXAMPLE 54

Preparation of Phosphoric acid,
ethyl-[2[[(4-(2,2,2-trifluoro ethoxy)-3-methyl-2-pyridinyl)methyl]sulfinyl]-1H-benzimidazole-1-yl]] methyl diester, sodium salt 1-chloromethyl-2[[(4-(2,2,2-trifluoroethoxy)-3-methyl-2-pyridinyl)methyl] sulfinyl]1-H-benzimidazole (40.5 mg, 0.1 mmol) and the di-tributylammonium salt of phosphoric acid mono ethyl ester (198 mg, 0.4 mmol) were mixed together with tributyl amine (19 mg, 0.1 mmol) and methylene chloride (10 ml). The solvent was evaporated and the residue heated on a water bath at 60° C. for 5 min. Methylene chloride was added, distilled off and the product was again heated for 5 minutes at 60° C. This procedure was repeated four times until the reaction was completed. The residue was dissolved in methylene chloride and washed with three portions of water. The organic layer was dried, filtered and evaporated. The crude mixture of tributylammonium salts was dissolved in methylene chloride and water was added. A solution of sodiumhydroxide was added until pH=10. The mixture was centrifuged and the aqueous layer washed with three portions of methylene chloride. Freeze drying gave the pure title compound as identified by NMR (Table 2).

EXAMPLE 57 AND 58

Preparation of a mixture of Phosphoric acid [6-methoxy-[2[[(4-isopropyloxy-2-pyridinyl)methyl]sulfinyl]-1H-benzimidazole-1-yl] methyl ester, dipotassium salt and Phosphoric acid [5-methoxy-[2[[(4-isopropyloxy-2-pyridinyl)methyl]sulfinyl]-1H-benzimidazole-1-yl]] methyl ester, dipotassium salt.

The title compounds were prepared as described in examples 29 and 32 but with potassium hydroxide instead of sodium hydroxide.

EXAMPLE 63 AND 64

Preparation of a mixture of Phosphoric acid,
methyl-[6-methoxy-[2[[(4-isopentyloxy-3,5-dimethyl-2-pyridinyl)methyl]sulfinyl]-1H-benzimidazole-1-yl] methyl diester, sodium salt and Phosphoric acid, methyl-[5-methoxy-[2[[(4-isopentyloxy-3,5-dimethyl-2-pyridinyl)methyl] sulfinyl]-1H-benzimidazole-1-yl] methyl diester, sodium salt.

The title compounds were prepared as described in example 54, but with the di-tributylammonium salt of phosphoric acid monomethyl ester.

EXAMPLE 67

This compound is identified in Table 1 and was prepared by method B as exemplified in Examples 63 and 64, with the exception that potassium hydroxide was used instead of sodium hydroxide.

EXAMPLES 75 AND 76

These compounds are identified in Table 1 and were prepared as exemplified in Example 54, with the exception that potassium hydroxide was used instead of sodium hydroxide.

EXAMPLE 165

This compound is identified in Table 1 and was prepared by method B as exemplified in Example 29, with the exception that the product was purified by chromatography on a reversed phase column instead of being washed with water.

EXAMPLE 166

Preparation of an isomeric mixture of phosphoric acid, 2-[[[(3,4-dimethoxy-2-pyridineyl)methyl]sulfinyl]-5 or 6-difluoromethoxy-1H-benzimidazole-1-yl]methyl ester, dipotassium salt.

1-chloromethyl-2-[[(3,4-dimethoxy-2-pyridinyl) methyl]sulfinyl]-5 or 6 difluoromethoxy-benzimidazole (17.5 mg, 40.5 μmmol.) in methylene chloride was mixed with ditributylammonium-salt of phosphoric acid (0.75 ml, 0.528 mmol.) in methylene chloride for 5 minutes. The solvent was evaporated and the residue heated on a water bath at 60° C. for 5 minutes. Then methylene chloride was added, distilled off and the product was heated another 5 minutes at 60° C. This procedure was repeated several times until the reaction was completed. The residue was dissolved in methylene chloride and washed four times with water. A solution of potassium hydroxide was added until pH 12 and the mixture was centrifuged, the layers separated and the aqueous layer washed with methylene chloride three times and then freeze dried.

EXAMPLE 167

Preparation of an isomeric mixture of phosphoric acid, methyl-[2-[[(3,4-di-methoxy-2-pyridinyl)methyl]-sulfinyl]5 or 6-difluoromethoxy-1H-benzimidazole-1-yl] methyl diester, sodium salt.

1-chloromethyl-2([[(3,4-dimethoxy-2-pyridinyl) methyl]sulfinyl]-5 or 6-difluoromethoxy-1H-benzimidazole, (17.5 mg. 40.5 μmol.) in methylene chloride was mixed with di-tributylammonium-salt of phosphoric acid, mono methyl ester in methylene chloride for five minutes. The solvent was evaporated and the residue heated on a waterbath at 60° C. for five minutes at 60° C. This procedure was repeated several times until the reaction was completed. The residue was dissolved in methylene chloride and washed three times with water. A solution of sodium hydroxide was added until pH 11. The mixture was centrifuged and the layers separated. The aqueous layer was then washed three times with methylene chloride and freeze dried.

PREPARATION OF INTERMEDIATES

2-[[(4-Methoxy-3,5-dimethyl-2-pyridinyl)methyl]-sulfinyl]-1H-benzimidazole-1-yl]] methanol 2-[[(4-Methoxy-3,5-dimethyl-2-pyridinyl)methyl]-sulfinyl]-1H-benzimidazole (3.15 g, 10 mmoles) and N,N-dimethylaminopyridine (120 mg, 1 mmol) was dissolved in methylene chloride (50 ml). A solution of formaldehyde (5M, 10 ml, 50 mmol) was added and the mixture was stirred violently for 2 minutes. The phases were separated and the methylene chloride solution was dried (sodium sulphate), filtered and evaporated to dryness. The slightly red residue was the title compound as an essentially pure oil.

NMR (500 MHz, CDCl$_3$,):2.15, 2.27, 3.70, 4,89, 5.89, 7.33, 7.63, 7.96

1-Hydroxymethyl-(5-methoxy) and 1-hydroxymethyl-(6-methoxy)-2-[[(4-methoxy-3,5-dimethyl-2-pyridinyl)methyl]sulfinyl]-1H-benzimidazole 5-methoxy-2-[[(4-methoxy-3,5-dimethyl-2-pyridinyl)-methyl]sulfinyl]-1H-benzimidazole (34.5 g 0.1 mol) was dissolved in methylenechloride (500 ml). A solution of formaldehyde (5M, 100 ml, 0.5 mol) was added and the mixture was stirred violently for 2 minutes. The phases were separated and the methylene chloride solution was dried (sodium sulfate) filtered and evaporated to dryness at low temperature (<30° C.). The slightly red residue was an isomeric mixture (ratio 1:2) of the title compounds and an essentially pure oil. This oil was used without purification in the subsequent reaction.

EXAMPLE I 12

1-Chloromethyl-2-[[(4-methoxy-3,5-dimethyl-2-pyridinyl)methyl]-sulfinyl]-1H-benzimidazole 2-[[(4-Methoxy-3,5-dimethyl-2-pyridinyl)methyl]-sulfinyl]-1H-benzimidazol-1-yl]-methonol (4.8 g, 14 mmoles) and triethyl amine (1.6 g, 15 mmoles) was dissolved in methylene chloride (100 ml). A solution of thionyl chloride (1.8 g, 15 mmoles) in methylene chloride (10 ml) was added with such a velocity that the reaction mixture refluxed gently. After 10 minutes at room temperature the methylene chloride was distilled off at reduced pressure and the residue was taken up in ethyl acetate (100 ml) and water (50 ml). The phases were separated and the ethyl acetate phase was dried over sodium sulphate and evaporated. Chromatography on silicia gel (ethyl acetate) gave the crystalline title compound which was recrystallized in a ethyl acetate/-diethyl ether mixture. Mp 140°-141° C. Yield 1.5 g (27%).

The compounds according to examples I 1–I 11, I 13–I 20, and I 23–I 39 Have been prepared by the method illustrated in example I 12.

EXAMPLES I 21 AND I 22

1-chloromethyl-(5-methoxy) and (6-methoxy)-2-[[(4-methoxy-3,5-dimethyl-2-pyridinyl) methyl]sulfinyl]-1H-benzimidazole 1-hydroxy methyl-(5-methoxy)and-(6-methoxy)-2-[[-(4-methoxy-3,5-dimethyl-2-pyridinyl) methyl]sulfinyl]-1H-benzimidazole (30 g 0.08 mol ratio 1:2) was dissolved in toluene (500 ml) and the solution was cooled to −30° C. A solution of thionyl chloride (19 g 0.16 mol) in toluene (100 ml) was added dropwise at −30° C. and the mixture was stirred for 10 minutes at −30° C. Then a solution of triethyl amine (45 g 0.45 mol) in toluene (200 ml) was added dropwise. After the addition the temperature was raised and the mixture stirred at room temperature for 30 minutes. The mixture was evaporated and the residue (120 g) was chromatographed on silica gel (ethylacetate-methylenechloride 50—50) giving the title compound as an isomeric mixture (ratio 1:3) Yield 11.9 g.

NMR (500 MHz, CDCl$_3$) 2.23, 2.25, 2.26, 3.72, 3.87, 3.92, 4.88, 4.95, 4.96, 6.17, 6.18, 6.54, 6.57, 6.95, 7.01, 7.19, 7.26, 7.43, 7.67, 8.17. If desired the pure 1-chloromethyl 6-methoxy-2-[[(4-methoxy-3,5-dimethyl- 2-pyridinyl)methyl]sulfinyl]-1H-benzimidazole was obtained when the isomeric mixture was crystallized in acetonitrile.

NMR (500 MHz, CDCl$_3$) 2.23, 2.25, 3.72, 3.92, 4.88, 4.96, 6.17, 6.57, 6.95, 7.01, 7.67, 8.17.

Preparation of Phosphoric acid, cyanoethyl-[6-methoxy-[-2-[[(4-methoxy-3,5-dimethyl-2-pyridinyl)methyl]sulfinyl]-1H-benzimidazole-1-yl]]methyl diester, triethylammonium salt (Method B)

1-Chloromethyl-6-methoxy-2[[(4-methoxy-3,5-dimethyl-2-pyridinyl)methyl]sulfinyl]-1H-benzimidazole (0.90 g, 0.0023 mol) was added under stirring to a solution of mono-triethylammonium salt of phosphoric acid cyanoethyl ester (0.70 g, 0.0028 mol) and triethyl amine (0.65 g, 0.0064 mol) in methylene chloride (20 ml). The mixture was refluxed overnight. The methylene chloride was distilled off and the residue was heated on a waterbath for 10 minutes at 60° C. and then used without further purification in the subsequent reaction.

Preparation of Phosphoric acid, dibenzyl-[2-[[(4-methoxy-3,5-dimethyl-2-pyridinyl)methyl]sulfinyl]-1H-benzimidazole-1-yl]methyltriester 1-Chloromethyl-2-[[(4-methoxy-3,5-dimethyl-2-pyridinyl)methyl]sulfinyl]-1H-benzimidazole (1.29 g, 3,5 mmoles) and the silversalt of phosphoric acid dibenzylester (1.79 g, 4,6 mmoles) was suspended in dry toluene. The mixture was heated on the water-bath at 90° C. for 3 hours, whereafter the toluene was distilled off at reduced pressure. The residue was taken up in methylene chloride (50 ml). Filtration (Hyflo) and evaporation of methylene chloride from the filtrate gave an oily product mixture which was chromatographed on silica gel (ethylacetate). Yield: 0,9 (42%) of the essentially pure title compound as an oil.

NMR (500 MHz, (CDCl$_3$δ): 2.20 (ds, 6H), 3.65 (s,3H), 4.8–5.0 (m,6H), 6.25–6.3 (m,1H), 6.45–6.5 (m,1H), 7.15–7.40 (m,12H), 7.65 (d,1H), 7.80 (d,1H), 8.1 (s,1H).

ISOMERIC FORMS

The isomeric identity of the pure example no. 29 was assigned by using NOE NMR techniques on its synthetic precursor no. I 22. All the other benzimidazole isomers have been structurally assigned by relating their NMR-spectra to that of example no. 29.

The preparation of the precursors no. I 21 and I 22 results in the formation of an isomeric mixture in the ratio 1:2. As a consequence, the target compounds no. 32 and 29 are formed as isomers in the same ratio 1:2. In the other examples, the isomeric ratios are sometimes different from 1:2 and are dependent on the substituents, especially the substituents on the benzimidazole nucleus.

A summary of the examples follows in Table 1 below.

TABLE 1

Summary of examples

| Ex. | X | R$^1$ | R$^2$ | R$^3$ | R$^4$ | D |
|---|---|---|---|---|---|---|
| 1 | SO | H | H | H | H | —O$_2$C—⟨piperidine⟩N—CH$_3$ |
| 2 | SO | H | H | H | H | —O$_2$C—⟨phenyl⟩—CH$_2$N(CH$_3$)$_2$ |
| 3 | SO | H | H | H | H | —O$_2$CCH$_2$CH$_2$CON⟨piperazine⟩N—CH$_3$ |
| 4 | SO | H | H | H | H | —O$_2$CCH$_2$CH$_2$CONCH$_2$CH$_2$N(CH$_2$CH$_3$)$_2$ with CH$_2$CH$_3$ on N |
| 5 | SO | H | H | H | H | —O$_2$C—⟨phenyl⟩—O$_2$CCH$_2$N(CH$_2$CH$_3$)$_2$ |
| 6 | SO | H | H | H | H | —O$_2$CCHO$_2$CCH$_2$N(CH$_2$CH$_3$)$_2$ with CH$_3$ branch |
| 7 | SO | H | H | H | H | —O$_2$CCH$_2$O$_2$CCH$_2$N(CH$_2$CH$_3$)$_2$ |

TABLE 1-continued
| | | | | | | |
|---|---|---|---|---|---|---|
| 8 | SO | H | H | H | H | $-O_2CCH_2N\diagup N-CH_3$ |
| 9 | SO | H | H | OCH$_3$ | H | 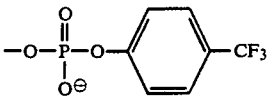 |
| 10 | SO | H | H | H | H | 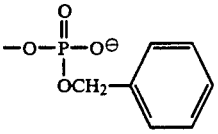 |
| 11 | SO | H | H | H | H | 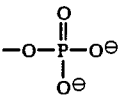 |
| 12 | SO | H | H | H | H | $-O_2COCH_2CH_2N(CH_3)_2$ |
| 13 | SO | H | H | H | H | 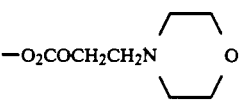 |
| 14 | SO | H | H | H | H | 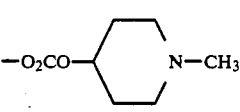 |
| 15 | SO | H | H | H | H | 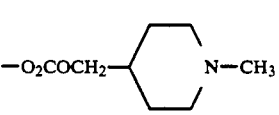 |
| 16 | SO | H | H | H | H | 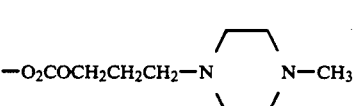 |
| 17 | SO | H | H | H | H | 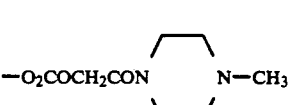 |
| 18 | SO | H | H | H | H | 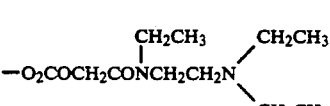 |
| 19 | SO | H | H | H | H | 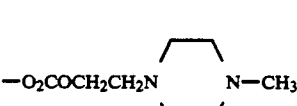 |
| 20 | SO | H | H | H | H | 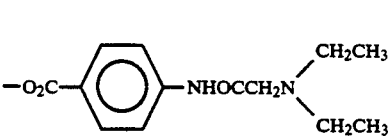 |

TABLE 1-continued
| | | | | | | |
|---|---|---|---|---|---|---|
| 21 | SO | H | H | H | H | 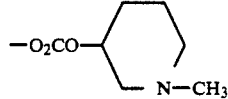 |
| 22 | SO | H | H | H | H | 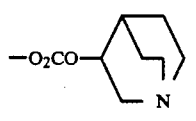 |
| 23 | SO | H | H | H | H | 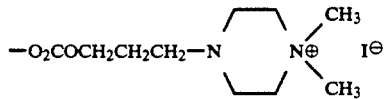 |
| 24 | SO | H | H | H | H | 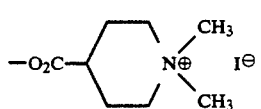 |
| 25 | SO | H | H | H | H | 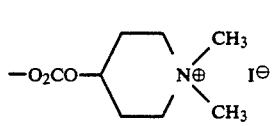 |
| 26 | SO | H | H | H | H | 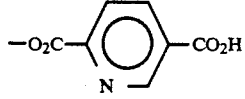 |
| 27 | SO | H | H | H | H | 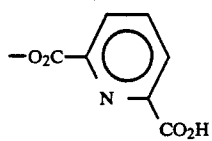 |
| 28 | SO | H | H | OCH$_3$ | H | 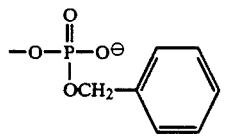 |
| 29 | SO | H | H | OCH$_3$ | H | 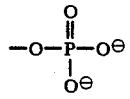 |
| 30 | SO | H | H | OCH$_3$ | H | 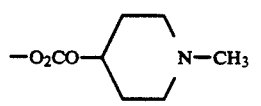 |
| 31 | SO | H | OCH$_3$ | H | H | 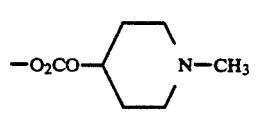 |
| 32 | SO | H | OCH$_3$ | H | H | 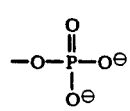 |
| 33 | SO | H | H | OCH$_3$ | H | 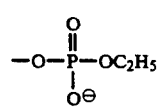 |

TABLE 1-continued
| | | | | | | |
|---|---|---|---|---|---|---|
| 34 | SO | H | OCH₃ | H | H | 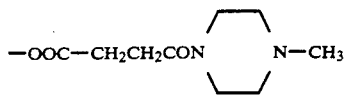 —OOC—CH₂CH₂CON⟨piperazine⟩N—CH₃ |
| 35 | SO | H | H | OCH₃ | H | 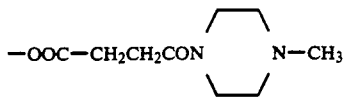 —OOC—CH₂CH₂CON⟨piperazine⟩N—CH₃ |
| 36 | SO | H | H | H | H | 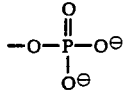 |
| 37 | SO | CH₃ | OCH₂CH₂OCH₃ | CH₃ | H | 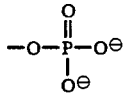 |
| 38 | SO | H | CH₃ | OCH₂CH₂OCH₃ | CH₃ | 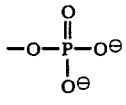 |
| 39 | SO | H | 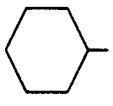 | H | H | 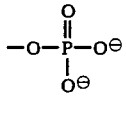 |
| 40 | SO | H | H | 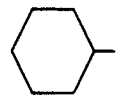 | H | 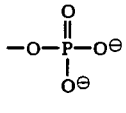 |
| 41 | SO | H | CO₂CH₃ | CH₃ | H | 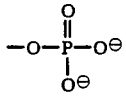 |
| 42 | SO | H | CH₃ | CO₂CH₃ | H | 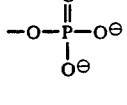 |
| 43 | SO | H | CH(CH₃)₂ | H | H | 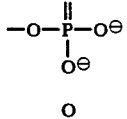 |
| 44 | SO | H | H | CH(CH₃)₂ | H | 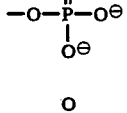 |
| 45 | SO | H | H | H | H | 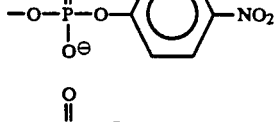 |
| 46 | SO | H | H | OCH₃ | H | 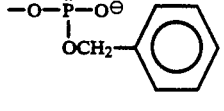 |
| 47 | SO | H | OCH₃ | H | H | 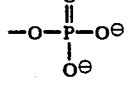 |

TABLE 1-continued

| # | | | | | | |
|---|---|---|---|---|---|---|
| 48 | SO | H | H | OCH₃ | H | $-O-\overset{\overset{O}{\|}}{\underset{\underset{O^{\ominus}}{\|}}{P}}-O^{\ominus}$ |
| 49 | SO | H | –C₆H₄– (phenyl) | H | H | $-O-\overset{\overset{O}{\|}}{\underset{\underset{O^{\ominus}}{\|}}{P}}-O^{\ominus}$ |
| 50 | SO | H | H | –C₆H₄– (phenyl) | H | $-O-\overset{\overset{O}{\|}}{\underset{\underset{O^{\ominus}}{\|}}{P}}-O^{\ominus}$ |
| 51 | SO | OCH₃ | H | H | OCH₃ | $-O-\overset{\overset{O}{\|}}{\underset{\underset{O^{\ominus}}{\|}}{P}}-O^{\ominus}$ |
| 52 | SO | H | Br | H | H | $-O-\overset{\overset{O}{\|}}{\underset{\underset{O^{\ominus}}{\|}}{P}}-O^{\ominus}$ |
| 53 | SO | H | H | Br | H | $-O-\overset{\overset{O}{\|}}{\underset{\underset{O^{\ominus}}{\|}}{P}}-O^{\ominus}$ |
| 54 | SO | H | H | H | H | $-O-\overset{\overset{O}{\|}}{\underset{\underset{O^{\ominus}}{\|}}{P}}-OCH_2CH_3$ |
| 55 | SO | H | Br | H | H | $-O-\overset{\overset{O}{\|}}{\underset{\underset{O^{\ominus}}{\|}}{P}}-OCH_2CH_3$ |
| 56 | SO | H | H | Br | H | $-O-\underset{\underset{O^{\ominus}}{\|}}{P(O)}OCH_2CH_3$ |
| 57 | SO | H | OCH₃ | H | H | $-O-\underset{\underset{O^{\ominus}}{\|}}{P(O)}-O^{\ominus}$ |
| 58 | SO | H | H | OCH₃ | H | $-O-\underset{\underset{O^{\ominus}}{\|}}{P(O)}O^{\ominus}$ |
| 59 | SO | CH₃ | OCH₂CH₂OCH₃ | CH₃ | H | $-O-\underset{\underset{O^{\ominus}}{\|}}{P(O)}OCH_2CH_3$ |
| 60 | SO | H | CH₃ | OCH₂CH₂OCH₃ | CH₃ | $-O-\underset{\underset{O^{\ominus}}{\|}}{P(O)}OCH_2CH_3$ |
| 61 | SO | H | –C₆H₄– (phenyl) | H | H | $-O-\underset{\underset{O^{\ominus}}{\|}}{P(O)}OCH_2CH_3$ |
| 62 | SO | H | H | –C₆H₄– (phenyl) | H | $-O-\underset{\underset{O^{\ominus}}{\|}}{P(O)}OCH_2CH_3$ |
| 63 | SO | H | OCH₃ | H | H | $-O-\underset{\underset{O^{\ominus}}{\|}}{P(O)}OCH_3$ |

TABLE 1-continued

| # | | | | | | |
|---|---|---|---|---|---|---|
| 64 | SO | H | H | OCH$_3$ | H | —O—P(O)OCH$_3$<br>\|<br>O$^\ominus$ |
| 65 | SO | H | OCH$_3$ | H | H | —O—P(O)O$^\ominus$<br>\|<br>O$^\ominus$ |
| 66 | SO | H | H | OCH$_3$ | H | —O—P(O)O$^\ominus$<br>\|<br>O$^\ominus$ |
| 67 | SO | H | $\begin{array}{c}CH_3\ \ \ CH_3\\ \ \ \ \|\ \ \ \ \ \|\\ CH_3-C-C-CH_3\\ \ \ \ \|\ \ \ \ \|\\ CH_3\ O\ \ CH_3\end{array}$ | | H | —O—P(O)O$^\ominus$<br>\|<br>OCH$_3$ |
| 68 | SO | H | $\begin{array}{c}CH_3\ \ \ CH_3\\ \ \ \ \|\ \ \ \ \ \|\\ CH_3-C-C-CH_3\\ \ \ \ \|\ \ \ \ \|\\ CH_3\ O\ \ CH_3\end{array}$ | | H | —O—P(O)$^\ominus$<br>\|<br>O$^\ominus$ |
| 69 | SO | H | CH$_2$CH$_2$OCH$_3$ | H | H | —O—P(O)O$^\ominus$<br>\|<br>O$^\ominus$ |
| 70 | SO | H | H | CH$_2$CH$_2$OCH$_3$ | H | —O—P(O)$^\ominus$<br>\|<br>O$^\ominus$ |
| 71 | SO | H | CH(CH$_3$)$_2$ | H | H | —O—P(O)O$^\ominus$<br>\|<br>OCH$_3$ |
| 72 | SO | H | H | CH(CH$_3$)$_2$ | H | —O—P(O)O$^\ominus$<br>\|<br>OCH$_3$ |
| 73 | SO | H | OCH$_3$ | H | H | O—P(O)O$^\ominus$<br>\|<br>OCH$_2$CH$_3$ |
| 74 | SO | H | H | OCH$_3$ | H | O—P(O)O$^\ominus$<br>\|<br>OCH$_2$CH$_3$ |
| 75 | SO | H | CH$_2$CH$_2$OCH$_3$ | H | H | —OP(O)CH$_2$CH$_3$<br>\|<br>O$^\ominus$ |
| 76 | SO | H | H | CH$_2$CH$_2$OCH$_3$ | H | —OP(O)OCH$_2$CH$_3$<br>\|<br>O$^\ominus$ |
| 77 | SO | H | OCH$_3$ | H | H | —OP(O)O$^\ominus$<br>\|<br>OCH$_2$—C$_6$H$_5$ |
| 78 | SO | H | OCF$_2$CHF$_2$ | H | H | O—P(O)$^\ominus$<br>\|<br>OCH$_2$CH$_3$ |
| 79 | SO | H | H | OCF$_2$CHF$_2$ | H | O—P(O)O$^\ominus$<br>\|<br>OCH$_2$CH$_3$ |
| 80 | SO | H | OCF$_2$CHF$_2$ | H | H | O—P(O)O$^\ominus$<br>\|<br>O$^\ominus$ |
| 81 | SO | H | H | OCF$_2$CHF$_2$ | H | O—P(O)O$^\ominus$<br>\|<br>O$^\ominus$ |

TABLE 1-continued

| # | | | | | | |
|---|---|---|---|---|---|---|
| 82 | S | H | H | H | H | $-OP(O)O^{\ominus}$<br>$\quad\;\;\,\vert$<br>$\quad\;\;O^{\ominus}$ |
| 83 | S | H | H | H | H | $-OP(O)OCH_2CH_3$<br>$\quad\;\;\,\vert$<br>$\quad\;\;O^{\ominus}$ |
| 84 | SO | H | $-OCH_2CH_2-C_6H_5$ | H | H | $-OP(O)OCH_3$<br>$\quad\;\;\,\vert$<br>$\quad\;\;O^{\ominus}$ |
| 85 | SO | H | H | $-OCH_2CH_2-C_6H_5$ | H | $-OP(O)OCH_3$<br>$\quad\;\;\,\vert$<br>$\quad\;\;O^{\ominus}$ |
| 86 | SO | H | $-CO-C_6H_5$ | H | H | $-OP(O)O^{\ominus}$<br>$\quad\;\;\,\vert$<br>$\quad\;\;O^{\ominus}$ |
| 87 | SO | H | H | $-CO-C_6H_5$ | H | $-OP(O)O^{\ominus}$<br>$\quad\;\;\,\vert$<br>$\quad\;\;O^{\ominus}$ |
| 88 | SO | H | $OCH_3$ | H | H | $-OP(O)O^{\ominus}$<br>$\quad\;\;\,\vert$<br>$\quad\;\;O^{\ominus}$ |
| 89 | SO | H | H | $OCH_3$ | H | $-OP(O)O^{\ominus}$<br>$\quad\;\;\,\vert$<br>$\quad\;\;O^{\ominus}$ |
| 90 | SO | H | H | $OCH_3$ | H | $-OOCCH_2CH_2CH_2CON\text{-piperazine-}N-CH_3$ |
| 91 | SO | H | H | H | H | $O-P(O)O^{\ominus}$<br>$\quad\;\;\,\vert$<br>$\quad\;\;O^{\ominus}$ |
| 92 | SO | H | H | H | H | $O-P(O)O^{\ominus}$<br>$\quad\;\;\,\vert$<br>$\quad\;\;O^{\ominus}$ |
| 93 | SO | H | H | H | H | $O-P(O)OC_2H_5$<br>$\quad\;\;\,\vert$<br>$\quad\;\;O^{\ominus}$ |
| 94 | SO | H | H | H | H | $O-P(O)O^{\ominus}$<br>$\quad\;\;\,\vert$<br>$\quad\;\;O^{\ominus}$ |
| 95 | SO | H | $OCH_3$ | F | H | $O-P(O)OC_2H_5$<br>$\quad\;\;\,\vert$<br>$\quad\;\;O^{\ominus}$ |
| 96 | SO | H | F | $OCH_3$ | H | $O-P(O)OC_2H_5$<br>$\quad\;\;\,\vert$<br>$\quad\;\;O^{\ominus}$ |
| 97 | SO | H | F | H | H | $O-P(O)O^{\ominus}$<br>$\quad\;\;\,\vert$<br>$\quad\;\;O^{\ominus}$ |
| 98 | SO | H | H | $OCH_3$ | H | $O-P(O)OCH_3$<br>$\quad\;\;\,\vert$<br>$\quad\;\;O^{\ominus}$ |
| 99 | SO | H | $-OCF_2O-$ | | H | $O-P(O)-O^{\ominus}$<br>$\quad\;\;\,\vert$<br>$\quad\;\;O^{\ominus}$ |

TABLE 1-continued

| | | | | | | |
|---|---|---|---|---|---|---|
| 100 | SO | H | —OCF$_2$O— | H | O—P(O)—O$^\ominus$ $\vert$ O$^\ominus$ | |
| 101 | SO | H | —OCF$_2$CHFO— | H | O—P(O)—O$^\ominus$ $\vert$ O$^\ominus$ | |
| 102 | SO | H | —OCHFCF$_2$O— | H | O—P(O)—OC$_2$H$_5$ $\vert$ O$^\ominus$ | |

| Ex. | R$^6$ | R$^7$ | R$^8$ | R$^9$ | Method (Ex. No.) | Yield % | Identifying data | Physical form |
|---|---|---|---|---|---|---|---|---|
| 1 | CH$_3$ | OCH$_3$ | CH$_3$ | H | A (1) | 8.5 | NMR | HBr-salt |
| 2 | CH$_3$ | OCH$_3$ | CH$_3$ | H | B (2) | 40 | NMR | Free base |
| 3 | CH$_3$ | OCH$_3$ | CH$_3$ | H | A (1) | 5 | NMR | HBr-salt |
| 4 | CH$_3$ | OCH$_3$ | CH$_3$ | H | | | | |
| 5 | CH$_3$ | OCH$_3$ | CH$_3$ | H | | | | |
| 6 | CH$_3$ | OCH$_3$ | CH$_3$ | H | | | | |
| 7 | CH$_3$ | OCH$_3$ | CH$_3$ | H | | | | |
| 8 | CH$_3$ | OCH$_3$ | CH$_3$ | H | | | | |
| 9 | CH$_3$ | OCH$_3$ | CH$_3$ | H | | | | |
| 10 | CH$_3$ | OCH$_3$ | CH$_3$ | H | (10) | 37 | NMR | Sodium salt |
| 11 | CH$_3$ | OCH$_3$ | CH$_3$ | H | B (29) | 20 | NMR | Sodium salt |
| 12 | CH$_3$ | OCH$_3$ | CH$_3$ | H | A (14) | 25 | NMR | Free base |
| 13 | CH$_3$ | OCH$_3$ | CH$_3$ | H | A (14) | 12 | NMR | Free base |
| 14 | CH$_3$ | OCH$_3$ | CH$_3$ | H | A (14) | 29 | NMR | HBr-salt |
| 15 | CH$_3$ | OCH$_3$ | CH$_3$ | H | A (14) | 14 | NMR | HBr-salt |
| 16 | CH$_3$ | OCH$_3$ | CH$_3$ | H | A (14) | 6 | NMR | HBr-salt |
| 17 | CH$_3$ | OCH$_3$ | CH$_3$ | H | | | | |
| 18 | CH$_3$ | OCH$_3$ | CH$_3$ | H | | | | |
| 19 | CH$_3$ | OCH$_3$ | CH$_3$ | H | | | | |
| 20 | CH$_3$ | OCH$_3$ | CH$_3$ | H | | | | |
| 21 | CH$_3$ | OCH$_3$ | CH$_3$ | H | | | | |
| 22 | CH$_3$ | OCH$_3$ | CH$_3$ | H | | | | |
| 23 | CH$_3$ | OCH$_3$ | CH$_3$ | H | 23 | 32 | NMR | |
| 24 | CH$_3$ | OCH$_3$ | CH$_3$ | H | | | | |
| 25 | CH$_3$ | OCH$_3$ | CH$_3$ | H | | | | |
| 26 | CH$_3$ | OCH$_3$ | CH$_3$ | H | | | | |
| 27 | CH$_3$ | OCH$_3$ | CH$_3$ | H | | | | |
| 28 | CH$_3$ | OCH$_3$ | CH$_3$ | H | | | | |
| 29 | CH$_3$ | OCH$_3$ | CH$_3$ | H | E (29) | 22 | NMR | Sodium salt |
| | | | | | B (29) | 35 | | Sodium salt |
| 30 | CH$_3$ | OCH$_3$ | CH$_3$ | H | | | | |
| 31 | CH$_3$ | OCH$_3$ | CH$_3$ | H | | | | |
| 32 | CH$_3$ | OCH$_3$ | CH$_3$ | H | B 32 | 1 | NMR | Sodium salt |
| 33 | CH$_3$ | OCH$_3$ | CH$_3$ | H | B (33) | 26 | NMR | Sodium salt |
| 34 | CH$_3$ | OCH$_3$ | CH$_3$ | H | A (34) | 56 | NMR | |
| 35 | CH$_3$ | OCH$_3$ | CH$_3$ | H | A (35) | | NMR | |
| 36 | CH$_3$ | OCH$_2$CF$_3$ | H | H | B (29) | | NMR | Sodium salt |
| 37 | H | CH$_3$ | CH$_3$ | H | B (29) | | NMR | Sodium salt |
| 38 | H | CH$_3$ | CH$_3$ | H | | | | |
| 39 | H | CH$_3$ | CH$_2$CH$_3$ | H | B (29) | | NMR | Sodium salt |
| 40 | H | CH$_3$ | CH$_2$CH$_3$ | H | B (29) | | NMR | Sodium salt |
| 41 | CH$_3$ | CH$_3$ | H | H | B (29) | | NMR | Sodium salt |
| 42 | CH$_3$ | CH$_3$ | H | H | B (29) | | NMR | Sodium salt |
| 43 | CH$_3$ | H | CH$_3$ | H | B (29) | | NMR | Sodium salt |
| 44 | CH$_3$ | H | CH$_3$ | H | B (29) | | NMR | Sodium salt |
| 45 | CH$_3$ | OCH$_3$ | CH$_3$ | H | B (45) | 10 | NMR | Sodium salt |
| 46 | CH$_3$ | OCH$_3$ | CH$_3$ | H | B (10) | | NMR | Sodium salt |
| 47 | CH$_3$ | OCH$_2$CH$_2$CH(CH$_3$)$_2$ | CH$_3$ | H | B (29) | | NMR | Sodium salt |
| 48 | CH$_3$ | OCH$_2$CH$_2$CH(CH$_3$)$_2$ | CH$_3$ | H | B (29) | | NMR | Sodium salt |
| 49 | CH$_3$ | OCH$_3$ | CH$_3$ | H | B (29) | | NMR | Sodium salt |
| 50 | CH$_3$ | OCH$_3$ | CH$_3$ | H | B (29) | | NMR | Sodium salt |
| 51 | CH$_3$ | OCH$_3$ | CH$_3$ | H | B (29) | | NMR | Sodium salt |
| 52 | CH$_3$ | OCH$_2$CH=CH$_2$ | CH$_3$ | H | B (29) | | NMR | Sodium salt |
| 53 | CH$_3$ | OCH$_2$CH=CH$_2$ | CH$_3$ | H | B (29) | | NMR | Sodium salt |
| 54 | CH$_3$ | OCH$_2$CF$_3$ | H | H | B (54) | | NMR | Sodium salt |
| 55 | CH$_3$ | OCH$_2$CH=CH$_2$ | CH$_3$ | H | B (54) | | NMR | Sodium salt |
| 56 | CH$_3$ | OCH$_2$CH=CH$_2$ | CH$_3$ | H | B (54) | | NMR | Sodium salt |
| 57 | H | O—CH(CH$_3$)$_2$ | H | H | B (57) | | NMR | Potassium salt |
| 58 | H | O—CH(CH$_3$)$_2$ | H | H | B (57) | | NMR | Potassium salt |
| 59 | H | CH$_3$ | CH$_3$ | H | B (54) | | NMR | Sodium salt |
| 60 | H | CH$_3$ | CH$_3$ | H | | | | |
| 61 | CH$_3$ | OCH$_3$ | CH$_3$ | H | B (54) | | NMR | Sodium salt |
| 62 | CH$_3$ | OCH$_3$ | CH$_3$ | H | B (54) | | NMR | Sodium salt |
| 63 | CH$_3$ | OCH$_2$CH$_2$CH(CH$_3$)$_2$ | CH$_3$ | H | B (63) | | NMR | Sodium salt |
| 64 | CH$_3$ | OCH$_2$CH$_2$CH(CH$_3$)$_2$ | CH$_3$ | H | B (63) | | NMR | Sodium salt |
| 65 | CH$_3$ | OCH$_2$CH$_2$OCH$_3$ | CH$_3$ | H | B (57) | | NMR | Potassium salt |
| 66 | CH$_3$ | OCH$_2$CH$_2$OCH$_3$ | CH$_3$ | H | B (57) | | NMR | Potassium salt |
| 67 | CH$_3$ | OCH$_3$ | H | H | B (67) | | NMR | Potassium salt |

TABLE 1-continued

| Ex. | X | R¹ | R² | R³ | R⁴ | | | |
|---|---|---|---|---|---|---|---|---|
| 68 | | CH₃ | OCH₃ | H | H | B (57) | NMR | Potassium salt |
| 69 | | CH₃ | OCH₃ | CH₃ | H | B (57) | NMR | Potassium salt |
| 70 | | CH₃ | OCH₃ | CH₃ | H | B (57) | NMR | Potassium salt |
| 71 | | CH₃ | H | CH₃ | H | B (67) | NMR | Potassium salt |
| 72 | | CH₃ | H | CH₃ | H | B (67) | NMR | Potassium salt |
| 73 | | CH₃ | OCH₂CH₂OCH₃ | CH₃ | H | B (54) | NMR | Sodium salt |
| 74 | | CH₃ | OCH₂CH₂OCH₃ | CH₃ | H | B (54) | NMR | Sodium salt |
| 75 | | CH₃ | OCH₃ | CH₃ | H | B (75) | NMR | Potassium salt |
| 76 | | CH₃ | OCH₃ | CH₃ | H | B (76) | NMR | Potassium salt |
| 77 | | CH₃ | OCH₃ | CH₃ | H | | | Sodium salt |
| 78 | | H | OCH₃ | H | H | | | Sodium salt |
| 79 | | H | OCH₃ | H | H | | | Sodium salt |
| 80 | | H | OCH₃ | H | H | | | Sodium salt |
| 81 | | H | OCH₃ | H | H | | | Sodium salt |
| 82 | | CH₃ | OCH₃ | CH₃ | H | B (57) | NMR | Potassium salt |
| 83 | | CH₃ | OCH₃ | CH₃ | H | B (54) | NMR | Sodium salt |
| 84 | | CH₃ | OCH₃ | CH₃ | H | B (67) | NMR | Potassium salt |
| 85 | | CH₃ | OCH₃ | CH₃ | H | B (67) | NMR | Potassium salt |
| 86 | | CH₃ | OCH₃ | CH₃ | H | B (57) | NMR | Potassium salt |
| 87 | | CH₃ | OCH₃ | CH₃ | H | B (57) | NMR | Potassium salt |
| 88 | | H | 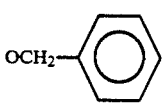 OCH₂-C₆H₅ | CH₂CH₃ | H | B (57) | NMR | Potassium salt |
| 89 | | H | 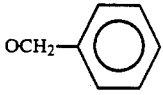 OCH₂-C₆H₅ | CH₂CH₃ | H | B (57) | NMR | Potassium salt |
| 90 | | CH₃ | OCH₃ | CH₃ | H | A (1) | NMR | HBr salt |
| 91 | | CH₃ | 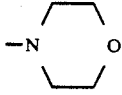 -N(morpholino)O | CH₃ | H | | | Potassium salt |
| 92 | | CH₃ | SC₂H₅ | H | H | | | Potassium salt |
| 93 | | CH₃ | SC₂H₅ | H | H | | | Potassium salt |
| 94 | | | —CH₂CH₂S— | H | H | | | Sodium salt |
| 95 | | H | OCH₃ | C₂H₅ | H | | | Sodium salt |
| 96 | | H | OCH₃ | C₂H₅ | H | | | Sodium salt |
| 97 | | H | OCH₃ | n-C₄H₉ | H | | | Potassium salt |
| 98 | | H | OCH₃ | n-C₅H₁₁ | H | | | Sodium salt |
| 99 | | H | OCH₃ | H | H | | | Sodium salt |
| 100 | | CH₃ | OCH₃ | H | H | | | Potassium salt |
| 101 | | CH₃ | OCH₃ | H | H | | | Potassium salt |
| 102 | | CH₃ | OCH₃ | H | H | | | Sodium salt |

Summary of examples

| Ex. | X | R¹ | R² | R³ | R⁴ | D |
|---|---|---|---|---|---|---|
| 103 | SO | H | | —OCF₂O— | H | —O—P(O)(O⁻)—OC₂H₅ |
| 104 | SO | H | H | OCF₃ | H | —O—P(O)(O⁻)—O⁻ |
| 105 | SO | H | H | OCF₃ | H | —O—P(O)(O⁻)O⁻ |
| 106 | SO | H | H | OCF₃ | H | —O—P(O)(O⁻)OCH₃ |
| 107 | SO | H | 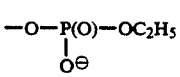 —SO₂O—C₆H₄—F | H | H | —O—P(O)(O⁻)—OC₂H₅ |

| No. | X | | | | | Group |
|---|---|---|---|---|---|---|
| 108 | S | H | H | —SO₂O—⟨C₆H₄⟩—F | H | $-O-P(O)(O^{\ominus})-OCH_3$ |
| 109 | SO | H | H | —NHSO₂—⟨C₆H₅⟩ | H | $-O-P(O)(O^{\ominus})-O^{\ominus}$ |
| 110 | SO | H | H | H | H | $-O-P(O)(O^{\ominus})-O^{\ominus}$ |
| 111 | SO | H | H | OCH₃ | H | $-O-P(O)(O^{\ominus})-O^{\ominus}$ |
| 112 | SO | H | H | H | H | $-O-P(O)(O^{\ominus})-O^{\ominus}$ |
| 113 | SO | H | H | H | H | $-O-P(O)(O^{\ominus})-OCH_3$ |
| 114 | SO | H | H | CH₃ | H | $-O-P(O)(O^{\ominus})OC_2H_5$ |
| 115 | SO | H | H | H | H | $-O-P(O)(O^{\ominus})O^{\ominus}$ |
| 116 | SO | H | H | CH₃ | H | $-O-P(O)(O^{\ominus})O^{\ominus}$ |
| 117 | SO | H | H | H | H | $-O-P(O)(O^{\ominus})OC_2H_5$ |
| 118 | SO | H | H | H | H | $-O-P(O)(O^{\ominus})-O^{\ominus}$ |
| 119 | SO | H | H | H | H | $-O-P(O)(O^{\ominus})-O^{\ominus}$ |
| 120 | SO | H | H | H | H | $-O-P(O)(O^{\ominus})-OC_2H_5$ |
| 121 | SO | H | H | OCH₃ | H | $-O-P(O)(O^{\ominus})-O^{\ominus}$ |
| 122 | SO | H | H | H | H | $-O-P(O)(O^{\ominus})-O^{\ominus}$ |
| 123 | SO | H | CF₃ | H | H | $-O-P(O)(O^{\ominus})-OC_2H_5$ |
| 124 | SO | H | H | CF₃ | H | $-O-P(O)(O^{\ominus})-OC_2H_5$ |
| 125 | SO | H | H | H | H | $-O-P(O)(O^{\ominus})-O^{\ominus}$ |
| 126 | SO | H | H | H | H | $-O-P(O)(O^{\ominus})-OCH_3$ |

-continued

| | | | | | | |
|---|---|---|---|---|---|---|
| 127 | SO | H | H | OCH₃ | H | —O—P(O)—OC₂H₅<br>\|<br>O⊖ |
| 128 | SO | H | OCH₃ | OCH₃ | H | —O—P(O)—OC₂H₅<br>\|<br>O⊖ |
| 129 | SO | H | H | OCH₃ | H | —O—P(O)—OCH₃<br>\|<br>O⊖ |
| 130 | SO | H | H | CF₃ | H | —O—P(O)—O⊖<br>\|<br>O⊖ |
| 131 | SO | H | CF₃ | H | H | —O—P(O)—O⊖<br>\|<br>O⊖ |
| 132 | SO | H | H | —OSO₂—C₆H₄—F | H | —O—P(O)—O⊖<br>\|<br>O⊖ |
| 133 | SO | H | H | —SO₂—O—C₆H₅ | H | —O—P(O)—O⊖<br>\|<br>O⊖ |
| 134 | SO | H | —OCF₂CHF— | | H | —O—P(O)O⊖<br>\|<br>O⊖ |
| 135 | S | H | —OCF₂CHF— | | H | —O—P(O)OC₂H₅<br>\|<br>O⊖ |
| 136 | SO | H | H | H | H | —O—P(O)O⊖<br>\|<br>O⊖ |
| 137 | SO | H | H | OCH₃ | H | —O—P(O)OC₂H₅<br>\|<br>O⊖ |
| 138 | SO | H | H | OCH₃ | H | —O—P(O)O⊖<br>\|<br>O⊖ |
| 139 | SO | H | H | OCH₃ | H | —O—P(O)O⊖<br>\|<br>O⊖ |
| 140 | SO | H | H | OCH₃ | H | —O—P(O)OC₃H₇<br>\|<br>O⊖ |
| 141 | SO | H | H | H | H | —O—P(O)OCH₃<br>\|<br>O⊖ |
| 142 | SO | H | —OCH₂O— | | H | —O—P(O)O⊖<br>\|<br>O⊖ |
| 143 | SO | H | —OCH₂O— | | H | —O—P(O)OC₂H₅<br>\|<br>O⊖ |
| 144 | SO | H | H | OCF₃ | H | —O—P(O)O⊖<br>\|<br>O⊖ |
| 145 | SO | H | H | OCH₃ | H | —O—P(O)OC₂H₅<br>\|<br>O⊖ |

-continued

| | | | | | | |
|---|---|---|---|---|---|---|
| 146 | SO | H | H | OCF$_3$ | H | —O—P(O)O$^\ominus$<br>\|<br>O$^\ominus$ |
| 147 | SO | H | OCF$_3$ | H | H | —O—P(O)O$^\ominus$<br>\|<br>O$^\ominus$ |
| 148 | SO | H | H | OCF$_2$CHF$_2$ | H | —O—P(O)O$^\ominus$<br>\|<br>O$^\ominus$ |
| 149 | SO | H | H | OCF$_3$ | H | —O—P(O)OCH$_2$—C$_6$H$_5$<br>\|<br>O$^\ominus$ |
| 150 | S | H | —OCF$_2$O— | | H | —O—P(O)OC$_2$H$_5$<br>\|<br>O$^\ominus$ |
| 151 | SO | H | —OCF$_2$O— | | H | —O—P(O)O$^\ominus$<br>\|<br>O$^\ominus$ |
| 152 | SO | H | OCF$_2$H | OCF$_2$H | H | —O—P(O)OC$_2$H$_5$<br>\|<br>O$^\ominus$ |
| 153 | SO | H | OCH$_3$ | OCF$_2$H | H | —O—P(O)OCH$_3$<br>\|<br>O$^\ominus$ |
| 154 | SO | H | H | OCF$_2$CF$_2$H | H | —O—P(O)O$^\ominus$<br>\|<br>O$^\ominus$ |
| 155 | SO | H | —OCF$_2$CFH— | | H | —O—P(O)O$^\ominus$<br>\|<br>O$^\ominus$ |
| 156 | SO | H | H | OCH$_3$ | H | —O—P(O)O$^\ominus$<br>\|<br>O$^\ominus$ |
| 157 | SO | H | H | OCF$_2$CHF$_2$ | H | —O—P(O)OCH$_3$<br>\|<br>O$^\ominus$ |
| 158 | SO | H | H | OCH$_3$ | H | —O—P(O)OCH$_3$<br>\|<br>O$^\ominus$ |
| 159 | SO | H | H | OCH$_3$ | H | —O—P(O)O$^\ominus$<br>\|<br>O$^\ominus$ |
| 160 | SO | H | OCH$_3$ | H | H | —O—P(O)O$^\ominus$<br>\|<br>O$^\ominus$ |
| 161 | SO | H | H | OCH$_3$ | H | —O—P(O)O$^\ominus$<br>\|<br>O$^\ominus$ |
| 162 | SO | H | H | OCH$_3$ | H | —O—P(O)OCH$_3$<br>\|<br>O$^\ominus$ |
| 163 | SO | H | H | OCH$_3$ | H | —O—P(O)OC$_2$H$_5$<br>\|<br>O$^\ominus$ |
| 164 | SO | H | H | OCH$_3$ | H | —O—P(O)—O$^\ominus$<br>\|<br>O$^\ominus$ |
| 165 | SO | H | H | OCH$_3$ | H | —O—P(O)—O—P—O$^\ominus$<br>\|       \|<br>O$^\ominus$    O$^\ominus$ |

-continued

| | | | | | | |
|---|---|---|---|---|---|---|
| 166 | SO | H | OCHF₂ | H | H | OP(O)—O⁻<br>      \|<br>      O⁻ |
| 167 | SO | H | OCHF₂ | H | H | OP(O)—O⁻<br>      \|<br>      OCH₃ |

| Ex. | R⁶ | R⁷ | R⁸ | R⁹ | Method (Ex. No.) | Yield % | Identifying data | Physical form |
|---|---|---|---|---|---|---|---|---|
| 103 | CH₃ | OCH₃ | H | H | | | | Sodium salt |
| 104 | H | OCH₃ | H | H | | | | Sodium salt |
| 105 | CH₃ | OCH₃ | H | H | | | | Sodium salt |
| 106 | H | OCH₃ | CH₃ | H | | | | Sodium salt |
| 107 | H | O(CH₂)₂OCH₃ | H | H | | | | Potassium salt |
| 108 | H | OCH₃ | H | H | | | | Potassium salt |
| 109 | H | OCH₃ | H | H | | | | Sodium salt |
| 110 | CH₃ | OCH₂-C₆H₄-F (4-F) | H | H | | | | Potassium salt |
| 111 | CH₃ | OCH₂-C₆H₅ | H | H | | | | Sodium salt |
| 112 | CH₃ | OCH₂-C₆H₄-CH₃ | H | H | | | | Sodium salt |
| 113 | CH₃ | OCH₂-C₆H₃-2,4-Cl₂ | H | H | | | | Sodium salt |
| 114 | CH₃ | OCH₂-C₆H₄-F | H | H | | | | Sodium salt |
| 115 | CH₃ | O-C₆H₅ | H | H | | | | Potassium salt |
| 116 | H | OCH₂-C₆H₄-F | CH₃ | H | | | | Potassium salt |
| 117 | CH₃ | OCH₂-C₆H₄-F | H | H | | | | Sodium salt |
| 118 | H | OCH₂CF₃ | H | H | | | | Sodium salt |
| 119 | CH₃ | OCH₂CF₂CF₃ | H | H | | | | Potassium salt |
| 120 | CH₃ | OCH₂CF₂CHF₂ | H | H | | | | Potassium salt |
| 121 | CH₃ | OCH₂CF₃ | H | H | | | | Sodium salt |
| 122 | H | O(CH₂)₂CH₃ | H | H | | | | Potassium salt |
| 123 | CH₃ | OCH₃ | H | H | | | | Sodium salt |
| 124 | CH₃ | OCH₃ | H | H | | | | Sodium salt |
| 125 | OCH₃ | OCH₃ | H | H | | | | Sodium salt |
| 126 | OCH₃ | O(CH₂)₂CH₃ | H | H | | | | Potassium salt |
| 127 | OCH₃ | OCH₃ | H | H | | | | Potassium salt |
| 128 | OCH₃ | OCH₃ | H | H | | | | Sodium salt |
| 129 | OCH₃ | OCH₂CF₃ | H | H | | | | Sodium salt |
| 130 | OCH₃ | OCH₃ | H | H | | | | Sodium salt |

-continued

| No | R1 | R2 | R3 | R4 | Salt |
|---|---|---|---|---|---|
| 131 | OCH$_3$ | OCH$_3$ | H | H | Sodium salt |
| 132 | CH$_3$ | OCH$_3$ | CH$_3$ | H | Potassium salt |
| 133 | CH$_3$ | OCH$_3$ | CH$_3$ | H | Sodium salt |
| 134 | CH$_3$ | OCH$_3$ | H | H | Sodium salt |
| 135 | CH$_3$ | OCH$_3$ | H | H | Potassium salt |
| 136 | H | SCH$_3$ | C$_2$H$_5$ | H | Sodium salt |
| 137 | H | OCH$_2$-C$_6$H$_5$ | C$_2$H$_5$ | H | Sodium salt |
| 138 | H | S-C$_6$H$_5$ | C$_2$H$_5$ | H | Potassium salt |
| 139 | H | O-C$_6$H$_5$ | C$_2$H$_5$ | H | Sodium salt |
| 140 | C$_2$H$_5$ | SC$_4$H$_9$ | H | H | Sodium salt |
| 141 | CH$_3$ | SCH$_3$ | H | H | Potassium salt |
| 142 | CH$_3$ | OCH$_3$ | H | H | Potassium salt |
| 143 | CH$_3$ | OCH$_3$ | CH$_3$ | H | Potassium salt |
| 144 | OCH$_3$ | OCH$_3$ | H | H | Potassium salt |
| 145 | C$_2$H$_5$ | OCH$_3$ | H | H | Potassium salt |
| 146 | OCH$_3$ | OCH$_3$ | H | H | Sodium salt |
| 147 | OCH$_3$ | OCH$_3$ | H | H | Sodium salt |
| 148 | OCH$_3$ | OCH$_3$ | H | H | Sodium salt |
| 149 | CH$_3$ | OCH$_3$ | OCH$_3$ | H | Sodium salt |
| 150 | H | OCH$_3$ | OCH$_3$ | H | Sodium salt |
| 151 | H | OCH$_3$ | OCH$_3$ | H | Sodium salt |
| 152 | CH$_3$ | OCH$_3$ | OCH$_3$ | H | Sodium salt |
| 153 | CH$_3$ | OCH$_3$ | CH$_3$ | H | Sodium salt |
| 154 | H | OCH$_3$ | OCH$_3$ | H | Sodium salt |
| 155 | H | OCH$_3$ | OCH$_3$ | H | Sodium salt |
| 156 | Cl | -N(piperidine) | CH$_3$ | H | Sodium salt |
| 157 | Cl | -N(piperidine) | CH$_3$ | H | Sodium salt |
| 158 | Cl | -N(morpholine) | H | H | Sodium salt |
| 159 | H | -N(piperidine) | Br | H | Sodium salt |
| 160 | Br | -N(piperidine) | H | H | Sodium salt |
| 161 | CH$_3$ | -N(piperidine) | Br | H | Sodium salt |

|     |     |     |     |     |       |     |              |
| --- | --- | --- | --- | --- | ----- | --- | ------------ |
| 162 | H   | —N(piperidinyl) | Br | H  |       |     | Sodium salt  |
| 163 | Cl  | —N(piperidinyl) | CH₃ | H |       |     | Sodium salt  |
| 164 | CH₃ | OCH₃ | CH₃ | CH₃ |       |     | Sodium salt  |
| 165 | CH₃ | OCH₃ | CH₃ | H   | B (29) | NMR | Sodium salt  |
| 166 | OCH₃ | OCH₃ | H | H   |       | NMR | Potassium salt |
| 167 | OCH₃ | OCH₃ | H | H   |       | NMR | Sodium salt  |

Identifying data for the compounds according to the examples in Table 1 are given in Table 2 below.

TABLE 2

| Ex. | Solvent | NMR data δ ppm (500 MHz) |
| --- | ------- | ------------------------ |
| 1 | DMSO-d₆ | 1.75 (q,2H), 2.0 (d,2H), 2.15 (s,3H), 2.20 (s,3H), 2.7 (m,5H), 2.9 (q,2H,), 3.65 (s,3H) 4.8–5.05 (dd,2H), 6.45 (s,2H), 7.35 (t,1H), 7.45 (t,1H), 7.8 (d,1H), 7.85 (d,1H), 8.15 (s,1H) |
| 2 | CDCl₃ | 2,20–2.25 (3s,12H), 3.45 (s,2H),3 3.70 (s,3H), 5.00 (s,2H,), 6.70 (dd,2H), 7.25–7.45 (m,4H), 7.75 (d,1H), 7.80 (d,1H) , 8.0 (d,2H) , 8.15 (s,1H) |
| 3 | CD₃OD | 2.3 (s,3H), 2.35 (s,3H), 2.7 (s,3H,), 2.7–3.0 (m,8H), 3.6–3.85 (m,4H), 3.8 (s,3H), 5.0–5.15 (dd,2H), 6.45–6.6 (dd,2H), 7.5 (t,1H), 7.55 (t,1H), 7.85 (d,2H), 8.2 (s,1H) |
| 10 | DMSO-d₆ | 2.15 (s,3H), 2.20 (s,3H), 3.65 (s,3H), 4.50–4.55 6.05–6.10 (m,1h), 7.10–7.40 (m,7H), 7.75 (d,1H), 7.85 (d,1H), 8.15 (s,1H) |
| 11 | D₂O | 2.00 (s,3H), 2.20 (s,3H), 3.50 (s,3H), 4.85–4.90 (m,1H), 5.00–5.05 (m,1H), 5.70–5.75 (m,1H), 5.80–5.85 (m,1H), 7.40–7.45 (m,1H), 7.50–7.55 (m,1H), 7.75 (d,1H), 7.80 (d,1H), 8.10 (s,1H) |
| 12 | CDCl₃ (90 MHz) | 2.23 (s,6H), 2.53 (t,2H), 3.66 (s,3H), 4.2 (t,2H), 4.91 (s,2H), 6.47 (dd,2H), 7.2–7.9 (m,4H), 8.12 (s,1H) |
| 13 | CDCl₃ | 2.2 (s,3H), 2.25 (s,3H), 2.5 (m,4H), 2.65 (m,2H), 3.6 (m,1H), 3.70 (s,3H), 4.3 (m,2H), 4.9–5.0 (dd,2H), 6.42–6.58 (dd,2H), 7.4 (t,1H), 7.45 (t,1H), 7.65 (d,1H), 7.85 (d,1H), 8.1 (s,1H) |
| 14 | CDCl₃ | 5.02 (dd,2H), 6.51 (dd,2H), 7.43 (dm,2H), 7.73 (dm,2H), 8.10 (s,1H) |
| 15 | CDCl₃ | 1.8–2.05 (m,5H), 2.2 (s,3H), 2.25 (s,3H), 2.75 (s,3H), 2.8 (d,2H), 3.5 (d,2H), 3.7 (s,3H), 4.0–4.1 (m,2H), 5.0 (dd,2H), 6.4–6.6 (dd,2H), 7.4 (t,1H), 7.45 (t,1H), 7.65 (d,1H), 7.8 (d,1H), 8.15 (s,1H) |
| 16 | CDCl₃ | 1.85 (t,2H), 2.25 (s,3H), 2.28 (s,3H), 2.50 (t,2H), 2.60 (s,3H), 2.75 (m,4H), 2.0 (m,4H), 3.75 (s,3H), 4.25 (m,2H), 4.95 (dd,2H), 6.5 (dd,2H), 7.4 (t,1H), 7.45 (t,1H), 7.65 (d,1H), 7.85 (d,1H), 8.1 (s,1H) |
| 23 | CDCl₃ | 1.8 (t,2H) 2.2 (s,3H), 2.24 (s,3H), 2.58 (m,2H), 2.75 (m,4H), 3.5 (s,6H), 3.6 (m,4H), 3.75 (s,3H), 4.26 (m,2H), 4.74 (dd,2H), 6.51 (dd,2H), 7.4 (t,1H), 7.45 (t,1H), 7.68 (d,1H), 7.85 (d,1H), 8.1 (s,1H) |
| 29 | D₂O | 2.0 (s,3H), 2.2 (s,3H), 3.5 (s,3H), 3.94 (s,3H), 4.85–4.9 (m,1H), 5.0–5.05 (m,1H), 5.65–5.7 (m,1H), 5.75–5.80 (m,1H), 7.05 (dd,1H), 7.35 (d,1H), 7.65 (d,1H), 8.1 (s,1H) |
| 32 | D₂O | 1.97 (s,3H) 2.16 (s,3H), 3,47 (s,3H), 3.87 (s,3H) 4.81–4.88 (m,1H) 4.97–5.02 (m,1H) 5.61–5.67 (m,1H), 5.70–5.75 (m,1H), 7.14 (dd,1H), 7.26 (d,1H) 7.78 (d,1H) 8.09 (s,1H) |
| 33 | D₂O | 0.85 (t,3H), 1.96 (s,3H) 2.16 (s,3H) 3.43 (s,3H), 3.39–3.59 (m,1H), 3.87 (s,3H) 4.78–4.90 (m,1H), 4.97–5.05 (m,1H), 5.64–5.75 (m,2H), 7.06 (dd,1H), 7.22 (d,1H) 7.67 (dd,1H) 8.10 (s,1H) |
| 34 | CDCl₃ | 2.21 (s,3H), 2.26 (s,3H) 2.29 (s,3H) 2.32 (t,2H,), 2.36 (t,2H 2.63 (t,2H), 2.69 (t,2H), 3.45 (t,2H), 3.57 (t,2H 3.70 (s,3H), 3.85 (s,3H), 4.93 (s,2H) 6.38 (d,1H), 6.46 (d,1H), 7.05 (dd,1H) 7.24 (d,1H) 7.51 (d,1H), 8.12 (s,1H) |
| 35 | COCl₃ | 2.21 (s,3H), 2.26 (s,3H), 2.29 (s,3H), 2.2 (t,2H), 2.36 (t,2H), 2.63 (t,2H), 2.69 (t,2H), 3.45 (t,2H), 3.57 (t,2H), 3.70 (s,3H), 3.90 (s,3H), 4.93 (s,2H) 6.39 (d,1H) 6.48 (d,1H), 6.97 (dd,1H) 7.08 (d,1H), 7.66 (d,1H), 8.12 (s,1H) |
| 36 | D₂O | 2.12 (s,3H), 4.63–4.73 (m,2H), 5.02(d,1H* 5.13 (d,1H)* 5.80–5.86 (m,1H), 5.87–5.97 (m,1H), 7.00 (d,1H) 7.52 (t,1H), 7.60(t,1H) 7.83 (d,1H) 7.99 (d,1H), 8.23 (d,1H) |
| 37 | D₂O | 1.85 (s,3H), 2.16 (s,3H), 2.39 (s,3H), 2.47 (s,3H) 3.52 (s,3H), 3.86–3.91 (m,2H), 4.05–4.10 (m,2H) 4.72 (d,1H)*, 4.80 (d,1H)*, 5.75 (dd,1H), 5.90 (dd,1H), 6.73 (s,1H), 7.56 (s,1H), 8.09 (s,1H) |
| 39 40 | D₂O | 1.12 (s,6H), 1.24–2.00 (m,20H), 1.99 (s,6H), 2.56 (q,4H), 2.66–2.80 (m,2H), 4.81–5.99 (m,4H)* 5.68 (dd1H), 5.76 (dd1H), 5.82 (dd1H), 5.91 (dd1H) 6.76 (s,1H), 6.77 (s,1H), 7.38 (d1H), 7.49 (d,1H) 7.55 (s,1H), 7.65 (d,1H), 7.69 (s,1H), 7.76 (d1H) 8.12 (s,1H), 8.14 (s,1H) |
| 41 | D₂O | 2.15 (s,3H), 2.25 (s,3H), 2.73 (s,3H), 4.01 (s,3H), 5.03 (d,1H)*, 5.10 (d,1H)*, 5.79 (dd,1H), 5.87 (dd,1H), 7.21 (d,1H), 7.80 (s,1H), 8.09 (s,1H), 8.29 (s,1H) |
| 42 | D₂O | 2.15 (s,3H), 2.25 (s,3H), 2.67 (s,3H), 4.03 (s,3H), 5.02 (d,1H)*, 5.09 (d,1H)*, 5.79 (dd,1H), 5.88 (dd,1H), 7.69 (s,1H), 7.72 (d,1H), 8.13 (d,1H), 8.38 (s,1H) |
| 43 44 | D₂O | 1.31 (d,6H), 1.33 (d,6H), 2.19 (s,6H), 2.25 (s,6H), 3.11 (m,1H), 3.13 (m,1H), 4.91 (d2H)*, 5.03 (d2H)*, 5.76–5.82 (m,2H), 5.82–5.99 (m,2H), 7.36 (d,2H), 7.42 (d,1H), 7.52 (dd,1H), 7.68 (d,1H), 7.72 (d,1H), 7.75 (d,1H), 7.79 (d,1H), 8.07 (d,1H), 8.08 (d,1H) |
| 45 | D₂O | 2.15 (s,3H), 2.18 (s,3H), 3.67 (s,3H), 4.67 (d,1H), 5.01 (d,1H), 6.05 (t,1H), 6.16 (t,1H), 7.10 (d,2H), 7.28 (t,1H), 7.33 (t,1H), 7.69 (d,1H), 7.73 (d,1H), 7.95 (d,2H), 8.16 (s,1H |
| 46 | D₂O | 1.95 (s,3H), 2.11 (s,3H), 3.45 (s,3H), 3.79 (s,3H), 4.48–4.49 (m,2H), 4.65 (s,1H), 4.88 (d,1H), 5.72 (t,1H), 5.80 (t,1H), 6.81 (d,2H), 6.97 (d,1H), 7.09–7.21 (m,4H), 7.57 (d,1H), 8.06 (s,1H) |
| 47 | D₂O | 0.87 (d,3H), 0.88 (d,3H), 1.47–1.57 (m,2H), 1.59–1.70 (m,1H), 1.91 (s,3H), 2.21 (s,3H), 3.20–3.27 (m,1H), 3.40–3.47 (m,1H), 3.95 (s,3H), 4.90 (d,1H)*, 5.10 (d,1H)*, 5.55–5.62 (m,1H), 5.65–5.72 (m,1H), 7.20 (dd,1H), 7.33 (d,1H), 7.73 (d,1H), 8.25 (s,1H) |
| 48 | D₂O | 0.87 (d,3H), 0.88 (d,3H), 1.47–1.57 (m,2H), 1.59–1.70 (m,1H), 1.90 (s,3H), 2.22 (s,3H), 3.20–3.27 (m,1H), 3.40–3.47 (m,1H), 3.97 (s,3H), 4.90 (d,1H)*, 5.09 (d.1H)*, 5.55–5.62 (m,1H), 5.65–5.72 (m,1H), 7.13 (dd,1H), 7.39 (d,1H), 7.73 (d,1H), 8.25 (s,1H) |
| 49 50 | D₂O | 2.00 (s,3H), 2.02 (s,3H), 2.18 (s,6H), 3.46 (s,6H), 5.0 (s,)*, 5.75–5.82 (m,2H), 5.88 (dd,2H), |

TABLE 2-continued

| Ex. | Solvent | NMR data δ ppm (500 MHz) |
|---|---|---|
| 51 | D₂O | 7.39–7.61 (m,7H) 7.65–7.92 (m,7H, 7.98 (s,1H), 8.07 (s,1H), 8.14 (s,1H), 8.15 (s,1H) |
| 52 | D₂O | 1.98 (s,3H), 2.24 (s,3H). 3.51 (s,3H), 3.98 (s,3H), 4.00 (s,3H), 5.1 (s)*, 5.89–5.93 (m,2H), 6.88 (d,1H), 6.96 (d,1H), 8.18 (s,1H) |
| 53 | | 2.02 (s,6H), 2.23 (s,6H), 4.00–4.07 (m,2H), 4.11–4.17 (m,2H), 4.93 (d,2H)*, 5.08 (d,2H)*, 5.33 (dd,4H), 5.66–5.75 (m,2H), 5.76–5.87 (m,2H), 5.95–6.05 (m,2H), 7.61 (dd 1H), 7.67 (dd,1H), 7.70 (d,1H), 7.78 (d,1H), 8.00 (d,1H), 8.10 (d,1H), 8.18 (s,2H) |
| 54 | D₂O | 0.85 (t,3H), 1.99 (s,3H), 3.42–3.58 (m,2H), 5.0 (s)*, 5.78 (dd,1H), 5.82 (dd,1H), 6.92 (d,1H), 7.45 (t,1H), 7.53 (t,1H), 7.72 (d,1H), 7.80 (d,1H), 8.16 (d,1H) |
| 55 56 | D₂O | 0.95 (t,6H), 2.10 (s,6H), 2.20 (s,6H), 3.50–3.72 (m,4H), 4.00–4.10 (m,2H), 4.10–4.20 (m,2H), 5.10 (s)*, 5.37 (d,d,4H), 5.66–5.75 (m,2H), 5.76–5.87 (m,2H), 5.95–6.05 (m,2H), 7.60–7.90 (m,4H), 8.07 (d,1H), 8.13 (d,1H), 8.18 (s,2H) |
| 57 58 | D₂O | 1.01 (d,6H), 1.02 (d,6H), 3.88 (s,3H), 3.93 (s,3H), 4.20 (m,2H), 5.0 (s)*, 5.65–5.73 (m,2H), 5.80–5.88 (m,2H), 6.67–7.13 (m,7H), 7.23–7.56 (m,3H), 8.23 (d,2H) |
| 59 | D₂O | 0.88 (t,3H), 1.76 (s,3H), 2.05 (s,3H), 2.35 (s,3H), 2.37 (s,3H), 3.46 (s,3H), 3.49–3.60 (m,2H), 3.79–3.80 (m,2H), 3.94–3.96 (m,2H), 4.62 (d,1H), 4.82 (d,1H), 5.65 (dd 1H), 5.78 (dd 1H), 6.60 (s,1H), 7.32 (s,1H), 8.03 (s,1H) |
| 61 62 | D₂O | 0.95 (t,6H), 207 (s,6H), 2.25 (s,6H), 3.48 (s,3H), 3.51 (s,3H), 3.45–3.58 (m,2H), 3.58–3.71 (m,2H), 5.2 (s)*, 5.76–5.93 (m,4H), 7.50–7.70 (m,6H), 7.79–7.93 (m,7H), 7.97 (d,1H), 8.04 (s,1H), 8.13 (s,1H), 8.22 (s,2H), |
| 63 | D₂O | 0.78 (d,3H), 0.80 (d,3H), 1.40 (t,2H), 1.55 (m,1H), 1.79 (s,3H), 2.10 (s,3H), 3.15 (d,3H), 3.85 (s,1H), 5.0 (s)*, 5.55 (dd,1H), 5.62 (dd,1H), 7.10 (dd,1H) 7.28 (d,1H), 7.54 (d,1H), 8.15 (s,1H) |
| 64 | D₂O | 0.78 (d,3H), 0.80 (d,3H), 1.40 (t,2H), 1.55 (m,1H), 1.79 (s,3H), 2.10 (s,3H), 3.15 (d,3H), 3.85 (s,1H), 5.0 (s)*, 5.55 (dd,1H), 5.62 (dd,1H), 7.02 (dd,1H), 7.17 (d,1H), 7.64 (d,1H), 8.15 (s,1H) |
| 65 | D₂O | 1.91 (s,3H), 2.14 (s,3H), 3.30 (s,3H), 3.44–3.62 (m,4H), 3.88 (s,3H), 4.82 (d,1H)*, 5.01 (d,1H)*, 5.56–5.66 (m,1H), 5.66–5.75 (m,1H), 7.13 (dd,1H), 7.24 (d,1H), 7.66 (d,1H), 8.12 (s,1H) |
| 66 | D₂O | 1.91 (s,3H), 2.14 (s,3H), 3.30 (s,3H), 3.44–3.62 (m,4H), 3.90 (s,3H), 4.82 (d,1H)*, 5.01 (d,1H)*, 5.56–5.66 (m,1H), 5.66–5.75 (m,1H), 7.03 (dd,1H), 7.31 (d,1H), 7.62 (d,1H), 8.12 (s,1H) |
| 67 | D₂O | 1.36 (s,3H), 1.40 (s,3H), 1.42 (s,3H), 1.44 (s,3H), 1.94 (s,3H), 3.18 (d,3H), 3.78 (s,3H), 5.0 (s)*, 5.82 (dd,1H), 5.85 (dd,1H), 6.88 (d,1H), 7.78 (s,1H), 7.86 (s,1H), (s,1H), 8.17 (d,1H) |
| 68 | D₂O | 1.38, (s,3H), 1.41 (s,3H), 1.43 (s,3H), 1.44 (s,3H), 1.97 (s,3H), 3.79 (s,3H), 5.0 (s)*, 5.75 (dd,1H), 5.84 (dd,1H), 6.88 (d,1H), 7.73 (s,1H), 7.86 (s,1H), 8.13 (s,1H) |
| 69 | D₂O | 1.98 (s,3H), 2.19 (s,3H), 2.97 (m,2H), 3.38 (s,3H), 3.47 (s,3H), 3.76–3.83 (m,2H), 5.04 (s)*, 5.69–5.80 (m,2H), 7.44 (d,1H), 7.65 (s,1H), 7.76 (s,1H), 8.14 (s,1H) |
| 70 | D₂O | 1.98 (s,3H), 2.19 (s,3H), 3.07 (m,2H), 3.38 (s,3H), 3.45 (s,3H), 3.76–3.87 (m,2H) 5.04 (s)*, 5.69–5.80 (m,2H), 7.36 (d,1H), 7.70 (s,1H), 7.72 (d,1H) 8.14 (s,1H) |
| 71 | D₂O | 1.26 (d,6H), 2.10 (s,3H), 2.18 (s,3H), 3.03 (m,1H), 3.20 (d,3H), 4.85 (d,1H)*, 5.01 (d,1H)*, 5.74–5.84 (m,2H), 7.26 (s,1H), 7.45 (d,1H), 7.65 (d,1H), 7.68 (s,1H), 8.05 (s,1H) |
| 72 | D₂O | 1.28 (d,6H), 2.10 (s,3H), 2.18 (s,3H), 3.07 (m,1H), 3.20 (d,3H), 4.85 (d,1H)*, 5.01 (d,1H)*, 5.74–5.84 (m,2H), 7.26 (s,1H), 7.36 (d,1H), 7.62 (s,1H), 7.72 (d,1H), 8.05 (s,1H) |
| 73 | D₂O | 0.88 (t,3H), 1.91 (s,3H), 2.13 (s,3H), 3.30 (s,3H), 3.46–3.57 (m,2H), 3.86 (s,3H), 5.00 (d)*, 5.64–5.75 (m,2H), 7.10 (d,1H), 7.27 (s,1H), 7.56 (d,1H), 8.12 (s,1H) |
| 74 | D₂O | 0.88 (t,3H), 1.90 (s,3H), 2.13 (s,3H), 3.30 (s,3H), 3.46–3.57 (m,2H), 3.87 (s,3H), 5.00 (d)*, 5.64–5.75 (m,2H) 7.03 (d,1H), 7.18 (s,1H), 7.63 (d,1H), 8.12 (s,1H) |
| 75 76 | D₂O | 0.93 (t,6H), 2.05 (s,6H), 2.26 (s,6H) 3.13 (t,2H), 3.14 (t,2H), 3.44 (s,6H), 3.47 (s,3H), 3.49 (s,3H), 3.47–3.69 (m,4H), 3.86 (t,4H), 5.13 (d)*, 5.74–5.85 (m,4H), 7.46 (d,1H), 7.51 (d,1H), 7.66 (s,1H), 7.73 (d,1H), 7.77 (s,1H), 7.84 (d,1H), 8.22 (s,2H) |
| 82 | D₂O | 2.11 (s,3H), 2.19 (s,3H), 3.65 (s,3H), 4.51 (s,2H), 5.80 (d,2H, 7.37 (t,1H) 7.42 (t,1H), 7.67 (d,1H), 7.73 (d,1H), 8.07 (s,1H) |
| 83 | D₂O | 0.90 It,3H), 2.03 (s,3H), 2.14 (s,3H), 3.56 (q,2H), 3.59 (s,3H), 4.43 (s,2H), 5.71 (d,1H), 7.27–7.38 (m,2H), 7.53 (d,1H), 7.63 (d,1H), 8.02 (s,1H) |
| 84 | D₂O | 1.93 (s,3H), 2.11 (s,3H), 3.03 (t,2H), 3.23 (d,3H) 3.36 (s,3H), 4.24 (t,2H), 4.86 (d,1H)*, 5.06 (d,1H)*, 5.65–5.75 (m,1H), 5.75–5.87 (m,1H), 7.04 (d,1H), 7.24 (s,1H), 7.27–7.48 (m,5H), 7.57 (d,1H), 8.12 (s,1H) |
| 85 | D₂O | 1.95 (s,3H), 2.13 (s,3H), 3.09 (t,2H), 3.23 (d,3H), 3.28 (s,3H), 4.34 (m,2H), 4.86 (d,1H)*, 5.06 (d,1H)*, 5.65–5.75 (m,1H), 5.75–5.87 (m,1H), 6.97 (d,1H), 7.20 (s,1H), 7.27–7.48 (m,5H), 7.65 (d,1H), 8.14 (s,1H) |
| 86 87 | D₂O | 2.09 (s,3H), 2.23 (s,3H), 3.60 (s,3H), 4.97 (d,1H)*, 5.09 (d,1H)*, 5.78–5.90 (m,1H), 5.90–6.03 (m,1H), 7.57–7.94 (m,5H), 7.99 (s,2H), 8.13 (s,1H), 8.17 (s,1H) |
| 88 89 | D₂O | 0.93 (t,6H), 2.34 (q,4H), 3.68 (s,3H), 3.72 (s,3H) 4.65 (s,4H), 5.1 (s)*, 5.50–5.84 (m,4H), 6.35 (s,2H), 6.58–7.52 (m,16H), 8.02 (s,2H) |
| 90 | D₂O | 1.76 (t,2H0, 2.01 (s,3H), 2.11 (t,2H), 2.42 (m,4H), 2.53 (s,3H), 2.65–3.83 (m,4H), 3.12 (t,2H), 3.46 (s,3H), 3.87 (s,3H), 4.81 (d,1H)*, 5.02 (d,1H)*, 5.95 (d,1H), 6.15 (d,1H), 7.05 (d,1H), 7.17 (s,1H), 7.87 (d,1H), 8.07 (s,1H) |
| 165 | D₂O | 2.00 (s,3H), 2.25 (s,3H), 3.50 (s,3H), 4.00 (s,3H), 4.95 (d,1H), 5.05 (d,1H), 5.95–6.00 (m,1H), 6.05–6.10 (m,1H), 7.15 (dd,1H), 7.45 (d,1H), 7.70 (d,1H), 8.20 (s,1H) |
| 166 | D₂O | 8.13 (s,1H), 8.15 (s,1H), 7.93 (d,1H), 7.81 (d,1H), 7.77 (d,1H), 7.62 (d,1H), 7.44 (d,1H), 7.34 (d,1H), 7.13 (s,1H), 7.12 (s,1H), 7.00 (t,1H), 6.93 (t,1H), 5.95–5.86 (m,2H), 5.03–4.83 (m,2H), 3.95 (s,3H), 3.80 (s,3H) |
| 167 | D₂O | 8.16 (s,1H), 8.15 (s,1H), 7.86 (d,1H), 7.83 (d,1H), 7.66 (d,1H), 7.65 (d,1H), 7.44 (dd,1H), 7.35 (dd,1H), 7.12 (s,1H), 7.11 (s,1H), 6.98 (t,1H), 6.94 (t,1H), 5.97–5.93 (m,2H), 5.05–4.78 (m,2H), 3.94 (s,3H), 3.78 (s,3H) |

*Protons exchange upon stayig in D₂O

A summary of examples of intermediate compounds I1-I39 is given in Table 3 below.

TABLE 3

Intermediates, summary of working examples I1-I39.

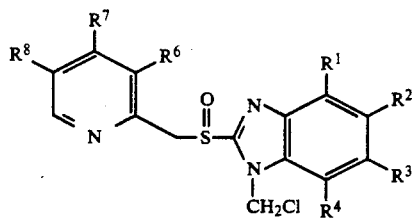

| Example | X | $R^1$ | $R^2$ | $R^3$ | $R^4$ | $R^6$ | $R^7$ | $R^8$ | Identifying data |
|---|---|---|---|---|---|---|---|---|---|
| I1 | SO | H | H | H | H | $CH_3$ | $OCH_2CF_3$ | H | NMR |
| I2 | SO | $CH_3$ | $OCH_2CH_2OCH_3$ | $CH_3$ | H | H | $CH_3$ | $CH_3$ | NMR |
| I3 | SO | H | $CH_3$ | $OCH_2CH_2OCH_3$ | $CH_3$ | H | $CH_3$ | $CH_3$ | |
| I4 | SO | H | cyclohexyl | H | H | H | $CH_3$ | $CH_2CH_3$ | NMR |
| I5 | SO | H | H | cyclohexyl | H | H | $CH_3$ | $CH_2CH_3$ | NMR |
| I6 | SO | H | $OCH_3$ | H | H | H | $OCH_2Ph$ | $CH_2CH_3$ | NMR |
| I7 | SO | H | H | $OCH_3$ | H | H | $OCH_2Ph$ | $CH_2CH_3$ | NMR |
| I8 | SO | H | $CO_2CH_3$ | $CH_3$ | H | $CH_3$ | $CH_3$ | H | NMR |
| I9 | SO | H | $CH_3$ | $CO_2CH_3$ | H | $CH_3$ | $CH_3$ | H | NMR |
| I10 | SO | H | $CH(CH_3)_2$ | H | H | $CH_3$ | H | $CH_3$ | NMR |
| I11 | SO | H | H | $CH(CH_3)_2$ | H | $CH_3$ | H | $CH_3$ | NMR |
| I12 | SO | H | H | H | H | $CH_3$ | $OCH_3$ | $CH_3$ | NMR |
| I13 | S | H | H | H | H | $CH_3$ | $OCH_3$ | $CH_3$ | NMR |
| I14 | SO | H | $OCH_3$ | H | H | $CH_3$ | $OCH_2CH_2CH(CH_3)_2$ | $CH_3$ | NMR |
| I15 | SO | H | H | $OCH_3$ | H | $CH_3$ | $OCH_2CH_2CH(CH_3)_2$ | $CH_3$ | NMR |
| I16 | SO | H | phenyl | H | H | $CH_3$ | $OCH_3$ | $CH_3$ | NMR |
| I17 | SO | H | H | phenyl | H | $CH_3$ | $OCH_3$ | $CH_3$ | NMR |
| I18 | SO | $OCH_3$ | H | H | $OCH_3$ | $CH_3$ | $OCH_3$ | $CH_3$ | NMR |
| I19 | SO | H | Br | H | H | $CH_3$ | $OCH_2CH=CH_2$ | $CH_3$ | NMR |
| I20 | SO | H | H | Br | H | $CH_3$ | $OCH_2CH=CH_2$ | $CH_3$ | NMR |
| I21 | SO | H | $OCH_3$ | H | H | $CH_3$ | $OCH_3$ | $CH_3$ | NMR |
| I22 | SO | H | H | $OCH_3$ | H | $CH_3$ | $OCH_3$ | $CH_3$ | NMR |
| I23 | SO | H | $OCH_3$ | H | H | H | $OCH(CH_3)_2$ | H | NMR |
| I24 | SO | H | H | $OCH_3$ | H | H | $OCH(CH_3)_2$ | H | NMR |
| I25 | SO | H | $OCF_3CF_2H$ | H | H | H | $OCH_3$ | H | NMR |
| I26 | SO | H | H | $OCF_3CF_2H$ | H | H | $OCH_3$ | H | NMR |
| I27 | SO | H | $CH_2OCOCH_3$ | H | H | $CH_3$ | $OCH_3$ | H | NMR |
| I28 | SO | H | H | $CH_2OCOCH_3$ | H | $CH_3$ | $OCH_3$ | H | NMR |

TABLE 3-continued
Intermediates, summary of working examples I1-I39.

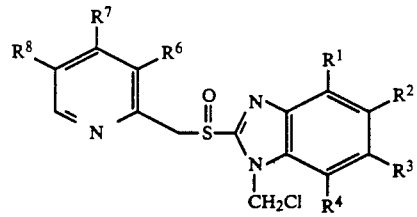

| Example | X | R¹ | R² | R³ | R⁴ | R⁶ | R⁷ | R⁸ | Identifying data |
|---|---|---|---|---|---|---|---|---|---|
| I29 | SO | H | | (CH₃)₃C-CO-C(CH₃)₃ | H | CH₃ | OCH₃ | H | NMR |
| I30 | SO | H | CH₂CH₂OCH₃ | H | H | CH₃ | OCH₃ | CH₃ | NMR |
| I31 | SO | H | H | CH₂CH₂OCH₃ | H | CH₃ | OCH₃ | CH₃ | NMR |
| I32 | SO | H | OCH₃ | H | H | CH₃ | OCH₂CH₂OCH₃ | CH₃ | NMR |
| I33 | SO | H | H | OCH₃ | H | CH₃ | OCH₂CH₂OCH₃ | CH₃ | NMR |
| I34 | SO | H | OCH₂-C₆H₅ | H | H | CH₃ | OCH₃ | CH₃ | NMR |
| I35 | SO | H | H | OCH₂-C₆H₅ | H | CH₃ | OCH₃ | CH₃ | NMR |
| I36 | SO | H | -CO-C₆H₅ | H | H | CH₃ | OCH₃ | CH₃ | NMR |
| I37 | SO | H | H | -CO-C₆H₅ | H | CH₃ | OCH₃ | CH₃ | NMR |
| I38 | SO | H | OCF₂CF₂H | H | H | H | OCH₃ | H | NMR |
| I39 | SO | H | H | OCF₂CF₂H | H | H | OCH₃ | H | NMR |

Identifying data for compunds according to examples I1-I39 are given in Table 4 below:

TABLE 4

| Ex. | Solvent | NMR data ppm (500 MHz) |
|---|---|---|
| I 1 | CDCl₃ | 2.27(s, 3H), 4.38(d, 1H), 4.41(d, 1H), 4.94(d, 1H), 5.03(d, 1H), 6.24(d, 1H), 6.60(d, 1H), 6.66(d, 1H), 7.41(t, 1H), 7.47(t, 1H), 7.57(d, 1H), 7.82(d, 1H), 8.30(d, 1H) |
| I 2 | CDCl₃ | 2.19(s, 3H), 2.23(s, 3H), 2.48(s, 3H), 2.57(s, 3H), 3.50(s, 3H), 3.76-3.78(m, 2H), 3.97-3.99(m, 2H), 4.75(d, 1H), 4.81(d, 1H), 6.10(d, 1H), 6.45(d, 1H), 7.05(s, 1H), 7.16(s, 1H), 8.29(s, 3H) |
| I 4 | | 1.20(t, 3H), 1.25-1.95(m, 11H), 2.21(s, 3H), |
| I 5 | | 2.60-2.64(m, 2H), 4.75-4.83(m, 2H), 6.14-6.18(m, 1H), 6.44-6.49(m, 1H), 7.03(d, 1H), 7.18(m, 1H), 7.26-7.45(m, 1H), 7.65-7.73(m, 1H), 8.31(s, 1H) |
| I 6 | CDCl₃ | 1.18(t, 3H), 2.61(q, 2H), 3.85(s, 3H), 4.78-4.82(m, 4H), 6.10(d, 1H), 6.39(d, 1H), 6.62(s, 1H), 6.94(d, 1H), 7.12(dd 1H), 7.32-7.43(m, 5H), 7.43(d, 1H), 8.24(s, 1H) |
| I 7 | CDCl₃ | 1.18(t, 3H), 2.61(q, 2H), 3.86(s, 3H), 4.78-4.82(m, 4H), 6.09(d, 1H), 6.41(d, 1H), 6.60(s, 1H), 6.94(d, 1H), 7.03(dd, 1H), 7.32-7.43(m, 5H), 7.71(d, 1H), 8.24(s, 1H) |
| I 8 | CDCl₃ | 2.29(s, 6H), 2.78(s, 3H), 3.93(s, 3H), 4.97-5.05(m, 2H), 6.19(d, 1H), 6.50(d, 1H), 7.00(d, 1H), 7.39(s, 1H), 8.18(d, 1H), 8.41(s, 1H) |
| I 9 | CDCl₃ | 2.29(s, 6H), 2.72(s, 3H), 3.96(s, 3H), 4.97-5.05(m, 2H), 6.21(d, 1H), 6.51(d, 1H), 7.00(d, 1H), 7.65(s, 1H), 8.16(s, 1H), 8.18(d, 1H) |
| I 10, I 11 | CDCl₃ | 1.32(d, 6H), 1.34(d, 6H), 2.27(s, 6H), 2.34(s, 6H), 3.08(m, 1H), 3.09(m, 1H), 4.86(d, 1H), 4.87(d, 1H), 4.96(d, 1H), 4.97(d, 1H), 6.19(d, 1H), 6.21(d, 1H), 6.54(d, 1H), 6.58(d, 1H), 7.28-7.74(m, 8H), 8.20(s, 2H) |
| I 12 | CDCl₃ | 2.22(s, 3H), 2.25(s, 3H), 3.71(s, 3H), 4.91(d, 1H), 4.97(d, 1H), 6.22(d, 1H), 6.59(d, 1H), 7.40(t, 1H), 7.46(t, 1H), 7.56(d, 1H), 7.82(d, 1H), 8.17(s, 1H) |
| I 13 | CDCl₃ | 2.26(s, 3H), 2.36(s, 3H), 3.79(s, 3H), 4.83(s, 2H), 5.94(s, 2H), 7.28-7.30(m, 2H), 7.39(dd, 1H), 7.70(dd, 1H), 8.23(s, 1H) |

TABLE 4-continued

| Ex. | Solvent | NMR data ppm (500 MHz) |
|---|---|---|
| I 14 | CDCl$_3$ | 0.97(d, 6H), 1.65-1.69(m, 2H), 1.81-1.84(m, 1H), 2.23(s, 3H), 2.24(s, 3H), 3.75-3.79(m, 2H), 3.86(s, 3H), 4.90(d, 1H), 4.95(d, 1H), 6.17(d, 1H), 6.51(d, 1H), 6.95(d, 1H), 7.10(dd, 1H), 7.43(d, 1H), 8.16(s, 1H) |
| I 15 | CDCl$_3$ | 0.97(d, 6H), 1.65-1.69(m, 2H), 1.81-1.84(m, 1H), 2.23(s, 3H), 2.24(s, 3H), 3.75-3.79(m, 2H), 3.91(s, 3H), 4.88(d, 1H), 4.96(d, 1H), 6.17(d, 1H), 6.54(d, 1H), 6.95(d, 1H), 7.01(dd 1H), 7.68(d, 1H), 8.16(s, 1H) |
| I 16 <br> I 17 | CDCl$_3$ | 2.23(s, 6H), 2.27(s, 3H), 2.28(s, 3H), 3.73(s, 6H), 4.95-4.97(m, 4H), 6.26(d, 1H), 6.27(d, 1H), 6.60(d, 1H), 6.63(d, 1H), 7.38-7.71(m, 14H), 7.87(d, 1H), 8.02(s, 1H), 8.18(s, 2H) |
| I 18 | CDCl$_3$ | 2.24(s, 3H), 2.27(s, 3H), 3.73(s, 3H), 3.97(s, 6H), 4.90(d, 1H), 5.05(d, 1H), 6.58(d, 1H), 6.65(d, 1H), 6.76(d, 1H), 6.83(d, 1H), 8.21(s, 1H) |
| I 19 <br> I 20 | CDCl$_3$ | 2.22(s, 6H), 2.25(s, 6H), 4.31(d, 4H), 4.91(d, 2H), 4.95(d, 2H), 5.28(d, 2H), 5.39(d, 2H), 6.03(m, 2H), 6.15(d, 1H), 6.18(d, 1H), 6.48(d, 1H), 6.50(d, 1H), 7.50(d, 1H), 7.53(d, 1H), 7.56(d, 1H), 7.67(d, 1H), 7.72(s, 1H), 7.95(s, 1H), 8.14(s, 2H) |
| I 21 | CDCl$_3$ | 2.23(s, 3H), 2.26(s, 3H), 3.72(s, 3H), 3.87(s, 3H), 4.89(d, 1H), 4.95(d, 1H), 6.18(d1H), 6.54(d, 1H), 7.19(dd, 1H), 7.26(d, 1H), 7.43(d, 1H), 8.17(d, 1H) |
| I 22 | CDCl$_3$ | 2.23(s, 3H), 2.25(s, 3H), 3.72(s, 3H), 3.92(s, 3H), 4.88(d, 1H), 4.96(d, 1H), 6.17(d, 1H), 6.57(d, 1H), 6.95(d, 1H), 7.01(dd 1H), 7.67(d, 1H), 8.17(s, 1H) |
| I 23 | CDCl$_3$ | 1.25(d, 6H), 3.87(s, 3H), 4.44(m, 1H), 4.82(dd, 2H), 6.13(d, 1H), 6.41(d, 1H), 6.71(d+s, 2H), 7.12(dd 1H), 7.26(d, 1H), 7.42(d, 1H), 8.35(d, 1H) |
| I 24 | CDCl$_3$ | 1.25(d, 6H), 3.92(s, 3H), 4.44(m, 1H), 4.82(dd, 2H), 6.13(d, 1H), 6.43(d, 1H), 6.71(d+s, 2H), 6.94(d, 1H), 7.02(dd, 1H), 7.69(d, 1H), 8.35(d, 1H) |
| I 25 <br> I 26 | CDCl$_3$ | 3.81(s, 6H), 4.84(dd, 4H), 5.97(m, 2H), 6.16(d, 1H), 6.18(d, 1H), 6.39(d, 1H), 6.41(d, 1H), 6.77(d+s, 4H), 7.30(dd, 1H), 7.34(dd 1H), 7.42(d, 1H), 7.54(d, 1H), 7.69(d, 1H), 7.81(d, 1H), 8.36(d, 2H) |
| I 27 <br> I 28 | CDCl$_3$ | 2.11(s, 6H), 2.22(s, 6H), 3.85(s, 6H), 4.99(m, 4H), 5.24(d, 2H), 5.27(d, 2H), 6.44(d, 2H), 6.50(d, 1H), 6.51(d, 1H), 6.68(d, 2H), 7.36(d, 1H), 7.42(d, 1H), 7.62(s, 2H), 7.79(d, 2H), 8.20(d, 2H) |
| I 29 | CDCl$_3$ | 1.40(s, 3H), 1.41(s, 3H), 1.44(s, 3H), 1.45(s, 3H), 2.50(s, 3H), 3.88(s, 3H), 4.95(d, 1H), 5.00(d, 1H), 6.28(d, 1H), 6.60(d, 1H), 6.74(d, 1H), 7.43(s, 1H), 7.70(s, 1H), 8.29(d, 1H) |
| I 30 <br> I 31 | CDCl$_3$ | 2.22(s, 6H), 2.25(s, 6H), 3.01-3.07(m, 4H), 3.36 3.37(s, 3H), 3.64-3.71(m, 4H), 3.71(s, 6H), 4.89(d, 2H), 4.95(d, 2H), 6.20(d, 2H), 6.56(d, 1H), 6.58(d, 1H), 7.28(d, 1H), 7.35(d, 1H), 7.41(s, 1H), 7.47(d, 1H), 7.67(s, 1H), 7.72(d, 1H), 8.17(s, 2H) |
| I 32 | CDCl$_3$ | 2.26(s, 3H), 2.28(s, 3H), 3.42(s, 3H), 3.66-3.69(m, 2H), 3.82(s, 3H), 3.85-3.93(m, 2H), 4.87-4.96(m, 2H), 6.17(d, 1H), 6.49(d, 1H), 7.08(dd, 1H), 7.25(d, 1H), 7.42(d, 1H), 8.16(s, 1H) |
| I 33 | CDCl$_3$ | 2.26(s, 3H), 2.28(s, 3H), 3.42(s, 3H), 3.66-3.69(m, 2H), 3.89(s, 3H), 3.85-3.93(m, 2H), 4.87-4.96(m, 2H), 6.17(d, 1H), 6.52(d, 1H), 6.98(d, 1H), 7.00(dd, 1H), 7.67(d, 1H), 8.16(s, 1H) |
| I 34 | CDCl$_3$ | 2.22(s, 3H), 2.24(s, 3H), 3.13(t, 2H), 3.71(s, 3H), 4.23(t, 2H), 4.88(d, 1H), 4.95(d, 1H), 6.16(d, 1H), 6.52(d, 1H), 7.09(dd, 1H), 7.25(d, 1H), 7.26-7.36(m, 5H), 7.41(d, 1H), 8.17(s, 1H) |
| I 35 | CDCl$_3$ | 2.22(s, 3H), 2.24(s, 3H), 3.16(t, 2H), 3.71(s, 3H), 4.26(t, 2H), 4.87(d, 1H), 4.96(d, 1H), 6.13(d, 1H), 6.52(d, 1H), 6.93(d, 1H), 7.01(dd, 1H), 7.26-7.36(m, 5H), 7.66(d, 1H), 8.17(s, 1H) |
| I 36 <br> I 37 | CDCl$_3$ | 2.23(s, 6H), 2.27(s, 6H), 3.74(s, 6H), 4.96-4.98(m, 4H), 6.25(d, 1H), 6.28(d, 1H), 6.55(d, 1H), 6.57(d, 1H), 7.48-7.87(m, 15H), 8.03(dd, 1H), 8.14(s, 1H), 8.23(s, 1H) |
| I 38 <br> I 39 | CDCl$_3$ | 3.74(s, 6H), 4.84(m, 4H), 5.86-6.08(m, 2H), 6.16(d, 1H), 6.18(d, 1H), 6.39(d, 1H), 6.41(d, 1H), 6.77(d+s, 4H), 7.29(dd, 1H), 7.35(dd, 1H), 7.42(d, 1H), 7.55(d, 1H), 7.69(d, 1H), 7.82(d, 1H), 8.36(d, 2H) |

Pharmaceutical preparations containing a compound of the invention as active ingredient are illustrated in the following formulations.

Syrup

A syrup containing 1% (weight per volume) of active substance was prepared from the following ingredients:

| Compound according to Example 29 | 1.0 g |
|---|---|
| Sugar, powder | 30.0 g |
| Saccharine | 0.6 g |
| Glycerol | 5.0 g |
| Flavouring agent | 0.05 g |
| Ethanol 96% | 5.0 g |
| Distilled water q.s. to a final volume of | 100 ml |

Sugar and saccharine were dissolved in 60 g of warm water. After cooling the active compound was added to the sugar solution and glycerol and a solution of flavouring agents dissolved in ethanol were added. The mixture was diluted with water to a final volume of 100 ml.

Enteric-coated Tablets

An enteric coated table containing 20 mg of active compound was prepared from the following ingredients:

| I | Compound according to Example 1 | 200 g |
|---|---|---|
| | Lactose | 700 g |
| | Methyl cellulose | 6 g |
| | Polyvinylpyrrolidone cross-linked | 50 g |
| | Magnesium stearate | 15 g |
| | Sodium carbonate | 6 g |
| | Distilled water | q.s. |

| II | Cellulose acetate phthalate | 200 g |
|---|---|---|
| | Cetyl alcohol | 15 g |
| | Isopropanol | 2000 g |
| | Methylene chloride | 2000 g |

I Compound according to example 5, powder, was mixed with lactose and granulated with a water solution of methyl cellulose and sodium carbonate. The wet mass was forced through a sieve and the granulate dried in an oven. After drying the granulate was mixed with polyvinylpyrrolidone and magnesium stearate. The dry mixture was pressed into tablet cores (10 000 tablets), each tablet containing 20 mg of active substance, in a tabletting machine using 6 mm diameter punches.

II A solution of cellulose acetate phthalate and cetyl alcohol in isopropanol/methylene chloride was sprayed onto the tablets I in an Accela Cota$^R$, Manesty coating equipment. A final tablet weight of 110 mg was obtained.

Solution for Intravenous Administration

A parenteral formulation for intravenous use, containing 4 mg of active compound per ml, was prepared from the following ingredients:

| Compound according to Example 1 | 4 g |
|---|---|
| Sterile water to a final volume of | 1000 ml |

The active compound was dissolved in water to a final volume of 1000 ml. The solution was filtered through a 0.22 μm filter and immediately dispensed into 10 ml sterile ampoules. The ampoules were sealed.

Tablets

Tablets containing 30 mg of active compound were prepared from the following ingredients:

| Compound according to Example 33 in Table 1 | 300 g |
|---|---|
| Lactose | 700 g |
| Methyl cellulose | 6 g |
| Polyvinyl pyrrolidone, cross-linked (PVP-XL) | 62 g |
| Disodium hydrogen phosphate | 2 g |
| Magnesium stearate | 30 g |
| Purified water | q.s. |

The active compound was mixed with lactose and part of the PVP-XL and granulated with a solution of methyl cellulose and disodium hydrogen phosphate. The wet mass was forced through a screen and dried in a fluidized bed dryer. After adding magnesium stearate and the remainder in PVP-XL and mixing, the drug mixture was compressed into tablets with a mean weight of 110 mg, each tablet containing 30 mg of the active compound.

Enteric Coated Tablets 500 g of the tablets above were enteric-coated. A solution of the composition below was sprayed onto the tablets in a fluidized bed apparatus using Wurster coating technique.

| Coating solution: | |
|---|---|
| Cellulose acetate phthalate | 40 g |
| Cetyl alcohol | 2 g |
| Isopropanol | 400 g |
| Dichloromethane | 400 g |

The final coated tablet weighed 117 mg.

Suppositories

Suppositories were prepared from the following ingredients using a welding procedure. Each suppository contained 40 mg of active compound.

| Compound according to Example 3 in Table 1 | 4 g |
|---|---|
| Witepsol H-15 | 180 g |

The active compound was homogenously mixed with Witepsol H-15 at a temperature of 41° C. The molten mass was volume filled into pre-fabricated suppository packages to a net weight of 1.84 g. After cooling the packages were heat sealed. Each suppository contained 40 mg of active compound.

Syrup

A syrup containing 1% of active substance was prepared from the following ingredients:

| Compound according to Example 33 in Table 1 | 1.0 g |
|---|---|
| Sugar, powder | 30.0 g |
| Saccharine | 0.6 g |
| Flavouring agent | 0.05 g |
| Ethanol 96% | 5.0 g |
| Purified water q.s. | to 100 ml |

Sugar and saccharine were dissolved in 60 g of warm water. After cooling the active compound was added to the sugar solution and a solution of flavouring agents dissolved in ethanol was added. The mixture was diluted with water to a final volume of 100 ml.

Solution for Intravenous or Intramuscular Injection

| Compound according to Example 29 in Table 1 | 60 g |
|---|---|
| Water for injection to make | 1000 ml |

The active compound was dissolved in water to a final volume of 1000 ml. The solution was filtered through a sterile 0.22 μm filter and aseptically dispensed into 1 ml sterile ampoules. The ampoules were sealed.

Formulation for Intravenous Infusion

| Sterile compound according to Example 29 in Table 1 | 60 mg |
|---|---|
| Sterile injection vials and stoppers | |

Sterile active compound, 60 mg, was dispensed into 10 ml sterile injection vials. The vials were stoppered with sterile rubber stoppers. The whole filling operation was performed under aspectic conditions in a sterile production area under vertical laminar flow.

Just before use, the active compound dissolved in 10 ml of sterile water is transferred into 100 ml of normal saline solution for infusion to give a total volume of about 110 ml. The solution is administered as an intravenous infusion during a time period of about 30 minutes.

BIOLOGICAL TESTS

Inhibiting Effect in Vivo on Gastric Acid Secretion in Conscious Dog

Test Method

Chronic gastric fistula dog were used. These dogs have been surgically provided with a gastric cannula in the stomach and a duodenal fistula, used for direct intraduodenal administration of test compounds. Following a 4 weeks' recovery period after surgery, tests were performed once a week on each dog. Food and water were withdrawn 18 hours before each test.

Gastric acid secretion was induced by a continuous 4 h infusion of histamine at individual doses (400–600 nmol/kg·h,iv) resulting in approximately 90% of maximal secretion of gastric acid. After 1 h of histamine stimulation, test compounds or vehicle were administered, either iv or im (vehicle=0.5% saline) or id (vehicle=0.5% Methocel®, 90 HG 15000, Dow Chem Corp.) via a catheter through the duodenal fistula. The gastric juice was collected by free flow from the gastric cannula in consecutive 30 min. samples during the duration of the histamine infusion. The samples were titrated to pH 7.0 with 0.1M or 1.0M NaOH using an automatic titrator and the acid output was calculated. The acid output during the periods after administration of test compound or vehicle was expressed as the fraction of the output during the period preceding these administrations, and the per cent inhibition of acid secretion was calculated by comparing in each dog the fractional responses induced by the test compound to the corresponding vehicle-induced fractional responses.

The test results given in Table 5 below represent inhibition during the 2nd hour after dose.

TABLE 5

Gastric acid inhibition in the dog

| Test compound Example no. | Administered dose $\mu$mol/kg | Route of administration | Inhibition of acid secretion (%) Number of dogs or experiments given within parentheses. |
|---|---|---|---|
| 29 | 0,3 | iv | 45 (1) |
|  | 0,5 | iv | 60 (1) |
|  | 1 | iv | 80–85 (2) |
|  | 1 | im | 90 (1) |
| Mixture of 29 and 32 (2:1) | 0,3 | iv | 55–64 (2) |
|  | 1 | iv | 98–98 (2) |
| 32 | 0,3 | iv | 55 (1) |
|  | 0,6 | iv | 53 (1) |
| 33 | 1 | id | 97 (1) |
|  | 4 | id | 98 (1) |
| 3 | 0,3 | iv | 72 (1) |
|  | 1 | iv | 98 (1) |
|  | 2 | id | 100 (1) |

Solubility

The solubility in water at room temperature for the compounds according to example 3 (HBr salt) and 29 (disodium salt) was measured and was shown to be higher than 60 mg per ml. By comparison, the sodium salt of omeprazole, 5-methoxy-2-[[(4-methoxy-3-5-dimethyl-pyridinyl)methyl] sulfinyl]-1-H-benzimidazole, has a solubility of 0.4 mg per ml at pH 9, a pH considered suitable for i.v. administration.

Chemical Stability

The chemical stability of various compounds of the invention have been followed kinetically at low concentration at 37° C. in aqueous buffer solution at different pH:es. The results shown in Table 6 below illustrate that the compounds of the invention have a high chemical stability.

TABLE 6

| Compound Example no. | t $\frac{1}{2}$ (hours) | | | | |
|---|---|---|---|---|---|
|  | pH 2 | pH 3 | pH 5 | pH 7.3 | pH 9.5 |
| Omeprazole-Na⊕[1)] | 0.07 |  | 0.04 | 20 |  |
| 3 |  |  | 112 | 32 |  |
| 29 |  |  |  | 74 | >>600[2)] |
| 32 |  |  |  | 51 |  |
| 33 |  |  | No decomp. after 30 h |  |  |
| 34 |  |  | 80 | 100 | 40 |

TABLE 6-continued

| Compound Example no. | t $\frac{1}{2}$ (hours) | | | | |
|---|---|---|---|---|---|
|  | pH 2 | pH 3 | pH 5 | pH 7.3 | pH 9.5 |
| 90 |  |  | 73 | 78 | 28 |

[1)]Omeprazole-Na⊕ = 5-methoxy-2-[[(4-methoxy-3,5-dimethyl-2-pyridinyl)-methyl]sulfinyl]-1H-benzimidazole sodium salt
[2)]12% decomposition after 25 days at 22° at the concentration 50 mg/ml

What we claim is:

1. A compound of the formula

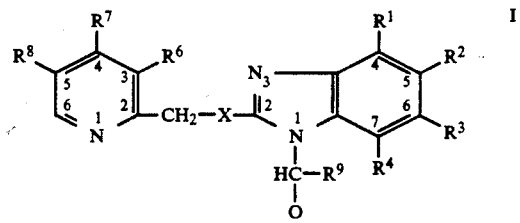

or a physiologically acceptable salt thereof, wherein
X is —S— or —SO—;
$R^1$, $R^2$, $R^3$ and $R^4$, which are the same or different, are
(a) H
(b) alkyl having 1-6 carbon atoms
(c) alkoxy having 1-6 carbon atoms
(d) alkoxyalkyl having 1-3 carbon atoms in both the alkoxy part and the alkyl part
(e) alkoxyalkoxy having 1-3 carbon atoms in each alkoxy part
(f) halogen
(g) —COR$^{10}$
(h) alkylthio having 1-6 carbon atoms in the alkyl part
(i) alkylsulfinyl having 1-7 carbon atoms in the alkyl part
(j) phenylalkyl or phenylalkoxy, having 1-6 carbon atoms in the alkyl or alkoxy parts
(k) phenyl or phenoxy
(l) OCHF$_2$
D is

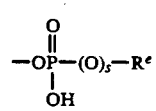

$R^6$ is
(a) H
(b) alkyl having 1-8 carbon atoms
(c) alkoxy having 1-8 carbon atoms
(d) halogen
$R^8$ is
(a) H
(b) alkyl having 1-8 carbon atoms
(c) alkoxy having 1-8 carbon atoms
(d) halogen
(e) phenylalkyl having 1-4 carbon atoms in the alkyl part
$R^7$ is alkoxy having 1-7 carbon atom
$R^9$ is
(a) H
(b) alkyl having 1-4 carbon atoms;
$R^{10}$ is
(a) alkyl having 1-4 carbon atoms
(b) alkoxy having 1-6 carbon atoms (c) phenyl;
$R^e$ is
(a) H
(b) (1-6C) alkyl
(c) benzyl
S is 1;
and whereby the group D preferably is in the form of a mono- or diionic salt containing a physiologically acceptable counter cation.

2. A compound according to claim 1 or a physiologically acceptable salt thereof, wherein $R^6$ is alkyl or alkoxy having 1-6 carbon atoms.

3. A compound according to claim 1 or a physiologically acceptable salt thereof, wherein $R^8$ is alkyl or alkoxy having 1-6 carbon atoms.

4. A compound according to claim 1 wherein X is SO.

5. A compound according to claim 1 wherein X is S.

6. A compound according to claim 1 wherein $R^1$, $R^2$, $R^3$ and $R^4$ are H, alkyl having 1-6 carbon atoms, or alkoxy having 1-6 carbon atoms.

7. A compound according to claim 1 wherein $R^1$, $R^2$, $R^3$ and $R^4$ all are H.

8. A compound according to claim 1 wherein $R^1$, $R^3$ and $R^4$ are H and $R^2$ is $OCH_3$ or $R^1$, $R^2$ and $R^4$ are hydrogen and $R^3$ is $OCH_3$.

9. A compound according to claim 1 wherein $R^9$ is H.

10. An alkali metal salt of a compound according to claim 1.

11. A compound according to claim 1 wherein the substituent in position 1 of the benzimidazole nucleus is $$-CH_2O\overset{\overset{O}{\|}}{\underset{\underset{OH}{|}}{P}}-OH$$

or an alkali metal salt thereof.

12. A compound according to claim 1 wherein the substituent in position 1 of the benzimidazole nucleus is $$-CH_2O\overset{\overset{O}{\|}}{\underset{\underset{OH}{|}}{P}}-OC_2H_5$$

or an alkali metal salt thereof.

13. A compound according to claim 1 wherein $R^9$ is H and D is $$-O-\overset{\overset{O}{\|}}{\underset{\underset{OCH_2-}{|}}{P}}-OH\text{—}\underset{}{\bigcirc}$$

14. A compound according to claim 1 wherein $R^6$, $R^7$ and $R^8$ are such that the pyridine ring of said compound is 3,5-dimethyl-4-methoxy-, 3-methyl-4-methoxy-, 5-ethyl-4-methoxy-, 4-methoxy-, 4-ethoxy-, 4-isopropoxy-, 3,4-dimethoxy-, 4,5-dimethoxy-, 3-methyl-4,5-dimethoxy-, 3-ethyl-4-methoxy-, 3-n-propyl-4-methoxy-, 3-isopropyl-4-methoxy-, or 3-t-butyl-4-methoxy-substituted.

15. A compound according to claim 1 wherein $R^6$, $R^7$ and $R^8$ are such that the pyridine ring of said compund is 3,5-dimethyl-4-methoxy-, 3-methyl-4-methoxy-, 3-ethyl-4-methoxy, 3-isopropyl-4-methoxy, 4-methoxy-, 4-ethoxy- or 4-isopropoxy-substituted.

16. A compound according to claim 1 wherein
X is SO
$R^1$, $R^2$, $R^3$ and $R^4$, which are the same or different, are
(a) H
(b) alkyl containing 1-4 carbon atoms
(c) alkoxy containing 1-4 carbon atoms
(d) alkoxyalkyl containing 1 or 2 carbon atoms in both the alkoxy part and the alkyl part
(e) alkoxyalkoxy containing 1 or 2 carbon atoms in each alkoxy part
(f) halogen
(g) alkanoyl containing 2-4 carbon atoms in the alkyl part
(h) phenylcarbonyl
(i) alkoxycarbonyl containing 1 or 2 carbon atoms in the alkoxy part
(j) phenylalkoxy containing 1-3 carbon atoms in the alkoxy part
(k) phenyl
(l) $OCHF_2$
$R^6$ and $R^8$ are $CH_3$
$R^7$ is $OCH_3$.

17. A compound according to claim 1 wherein the pyridinylmethylsulfinyl benzimidazole moiety is selected from the group consisting of

[structure 1]

[structure 2]

[structure 3]

18. A compound of the formula

[structure 4]

or a mono- or di-ionic salt thereof consisting of the compound and a physiologically acceptable counter cation, wherein $R_2$ and $R_3$ are combined as follows:

| $R^2$ | $R^3$ |
|---|---|
| H | OCH$_3$ |
| OCH$_3$ | H |

19. A method for inhibiting gastric acid secretion in mammals, which comprises administering to a host in need of such treatment an effective amount of a compound as defined in any one of claims 4, 5, 6–8, 9, 10–18 or 1.

20. A method for the treatment of gastrointestinal inflammatory diseases in mammals, which comprises administering to a host in need of such treatment an effective amount of a compound as defined in any one of claims 4, 5, 6–8, 9, 10–18 or 1.

21. A pharmaceutical composition for the treatment of gastrointestinal inflammatory diseases comprising an effective amount of a compound according to any one of claims 4, 5, 6–8, 9, 10–18, or 1 and a pharmaceutically acceptable carrier.

22. A pharmaceutical composition for the inhibition of gastric acid secretion comprising an effective amount of a compound according to any one of claims 4, 5, 6–8, 9, 10–18, or 1 and a pharmaceutically acceptable carrier.

* * * * *